(12) United States Patent
Thiel et al.

(10) Patent No.: US 10,751,100 B2
(45) Date of Patent: Aug. 25, 2020

(54) BONE SCREWS AND SURGICAL SETS COMPRISING BONE SCREWS

(71) Applicant: MEDARTIS HOLDING AG, Basel (CH)

(72) Inventors: Dirk Thiel, Staufen (DE); Andreas Mullis, Hemmiken (CH); Juergen Schonhardt, Rheinfelden (DE); Hermann Zeuner, Freiburg (DE); Simon Martin Schaetzle, Gottenheim (DE)

(73) Assignee: MEDARTIS HOLDING AG, Basel (CH)

( * ) Notice: Subject to any disclaimer, the term of this patent is extended or adjusted under 35 U.S.C. 154(b) by 134 days.

(21) Appl. No.: 15/820,702

(22) Filed: Nov. 22, 2017

(65) Prior Publication Data
US 2018/0103990 A1 Apr. 19, 2018

Related U.S. Application Data

(63) Continuation-in-part of application No. 15/536,430, filed as application No. PCT/EP2014/078136 on Dec. 17, 2014.

(51) Int. Cl.
*A61B 17/86* (2006.01)
*A61B 17/80* (2006.01)
(Continued)

(52) U.S. Cl.
CPC ........ *A61B 17/8625* (2013.01); *A61B 17/683* (2013.01); *A61B 17/8052* (2013.01);
(Continued)

(58) Field of Classification Search
CPC .............. A61B 17/8625; A61B 17/863; A61B 17/8047; A61B 17/8052; A61B 17/8057; A61B 17/8071
See application file for complete search history.

(56) References Cited

U.S. PATENT DOCUMENTS

| 4,726,808 | A | 2/1988 | Collins |
| 4,903,691 | A | 2/1990 | Heinl |

(Continued)

FOREIGN PATENT DOCUMENTS

| CH | 669 105 A5 | 2/1989 |
| CH | 675 531 A5 | 10/1990 |

(Continued)

OTHER PUBLICATIONS

US 9,125,700 B2, 09/2015, Olms et al. (withdrawn)
(Continued)

*Primary Examiner* — Matthew J Lawson
(74) *Attorney, Agent, or Firm* — Davis & Bujold PLLC; Michael J. Bujold

(57) ABSTRACT

A bone screw comprising a first end having an engagement contour for engaging with a tool to facilitate insertion or removal of the bone screw, and a blocking element is arranged at a second end thereof. The blocking element is provided with a circumferential outside surface which comprises at least one clamping surface which—when viewed in an azimuth plane perpendicular to a longitudinal axis of the bone screw—widens outwardly in a wedge-shaped manner away from the longitudinal axis. The bone plate includes at least one opening which is at least partially delimited by an inside wall having an inner contour for receiving and fixing the blocking element of the bone screw. At least one bone screw and at least one bone plate together form a surgical set.

12 Claims, 27 Drawing Sheets

Figure 1:
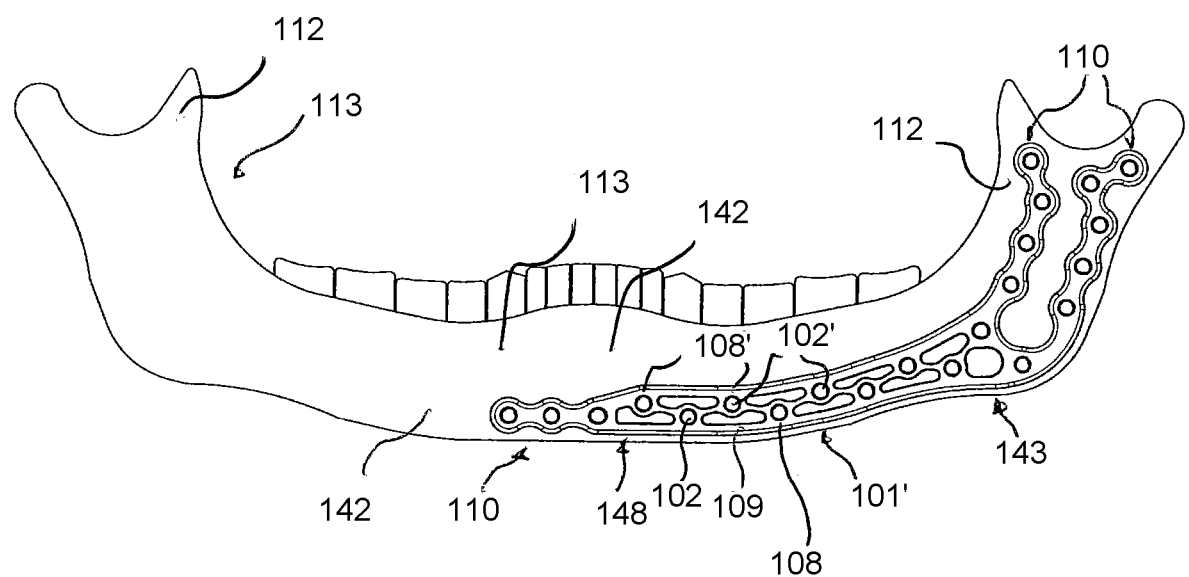

(51) Int. Cl.
*A61B 17/84* (2006.01)
*A61B 17/68* (2006.01)
*A61B 17/72* (2006.01)

(52) U.S. Cl.
CPC ...... *A61B 17/8071* (2013.01); *A61B 17/8085* (2013.01); *A61B 17/846* (2013.01); *A61B 17/848* (2013.01); *A61B 17/863* (2013.01); *A61B 17/864* (2013.01); *A61B 17/8605* (2013.01); *A61B 17/8665* (2013.01); *A61B 17/725* (2013.01); *A61B 17/8061* (2013.01)

(56) References Cited

U.S. PATENT DOCUMENTS

| | | | |
|---|---|---|---|
| 5,674,222 | A | 10/1997 | Berger et al. |
| 6,129,728 | A | 10/2000 | Schumacher et al. |
| 6,506,191 | B1 | 1/2003 | Joos |
| 6,730,091 | B1 | 5/2004 | Pfefferle et al. |
| 6,960,211 | B1 | 11/2005 | Pfefferle et al. |
| 8,292,898 | B2 | 10/2012 | Castaneda et al. |
| 8,672,981 | B2 | 3/2014 | Jacobs |
| 8,911,482 | B2 | 12/2014 | Lee et al. |
| 9,066,733 | B2 | 6/2015 | Furrer et al. |
| 9,066,767 | B2 | 6/2015 | Buchbinder et al. |
| 9,155,577 | B2 | 10/2015 | Pfefferle et al. |
| 2005/0090825 | A1 | 4/2005 | Pfefferle et al. |
| 2005/0234472 | A1 | 6/2005 | Carlucci et al. |
| 2005/0245933 | A1* | 11/2005 | Sevrain .................. A61B 17/68 606/286 |
| 2007/0238069 | A1 | 10/2007 | Lovald et al. |
| 2008/0275510 | A1* | 11/2008 | Schonhardt ........ A61B 17/8047 606/286 |
| 2009/0138051 | A1* | 5/2009 | Olms .................... A61B 17/683 606/280 |
| 2009/0281543 | A1 | 11/2009 | Orbay et al. |
| 2009/0299369 | A1 | 12/2009 | Orbay et al. |
| 2009/0312802 | A1 | 12/2009 | DaSilva |
| 2011/0046682 | A1* | 2/2011 | Stephan ............... A61B 17/686 606/305 |
| 2011/0118742 | A1* | 5/2011 | Hulliger ............. A61B 17/8047 606/70 |
| 2011/0144698 | A1 | 6/2011 | Buchbinder et al. |
| 2012/0010668 | A1* | 1/2012 | Shimko .............. A61B 17/7032 606/305 |
| 2013/0096559 | A1 | 4/2013 | Katrana et al. |
| 2013/0245697 | A1* | 9/2013 | Hulliger ................. A61B 17/84 606/281 |

FOREIGN PATENT DOCUMENTS

| | | |
|---|---|---|
| DE | 36 01 715 A1 | 7/1987 |
| DE | 103 35 281 A1 | 7/2004 |
| DE | 10 2010 048 052 A1 | 4/2012 |
| DE | 10 2014 107 495 A1 | 12/2015 |
| EP | 1 182 972 B1 | 10/2003 |
| EP | 1 107 699 B1 | 11/2003 |
| EP | 1 468 656 A1 | 10/2004 |
| EP | 2 792 324 A1 | 10/2014 |
| FR | 2622431 A1 | 5/1989 |
| JP | 2003509093 A | 3/2003 |
| JP | 2003530138 A | 10/2003 |
| JP | 2009500093 A | 1/2009 |
| JP | 2012502687 A | 2/2012 |
| JP | 2013513438 A | 4/2013 |
| JP | 2013524995 A | 6/2013 |
| RU | 2 033 105 C1 | 4/1995 |
| WO | 00/66012 A1 | 11/2000 |
| WO | 01/82809 A1 | 11/2001 |
| WO | 03/068091 A1 | 8/2003 |
| WO | 2004/086990 A1 | 10/2004 |
| WO | 2010/080511 A1 | 7/2010 |
| WO | 2013/096592 A1 | 6/2013 |

OTHER PUBLICATIONS

Japanese Office Action issued in corresponding Japanese Patent Application No. 2017-532957 dated Oct. 2, 2018.
International Search Report Corresponding to PCT/EP2014/078136 dated Oct. 7, 2015.
Supplemental Search Report Corresponding to PCT/EP2017/078136 dated Aug. 20, 2015.
Written Opinion Corresponding to PCT/EP2014/078136 dated Oct. 7, 2015.
European Search Report issued in corresponding European Patent Application No. EP 19 20 3806 dated Jan. 28, 2020.

* cited by examiner

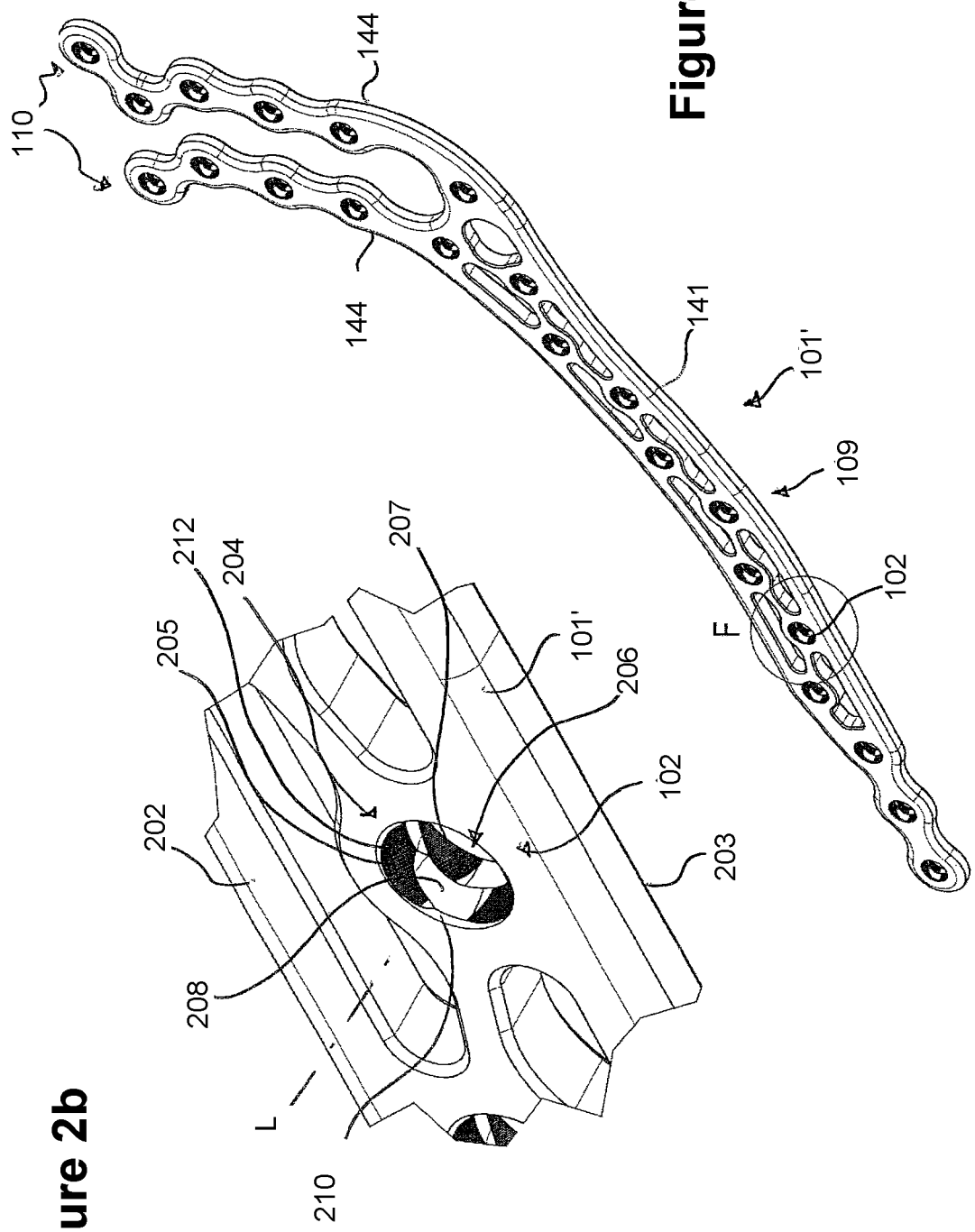

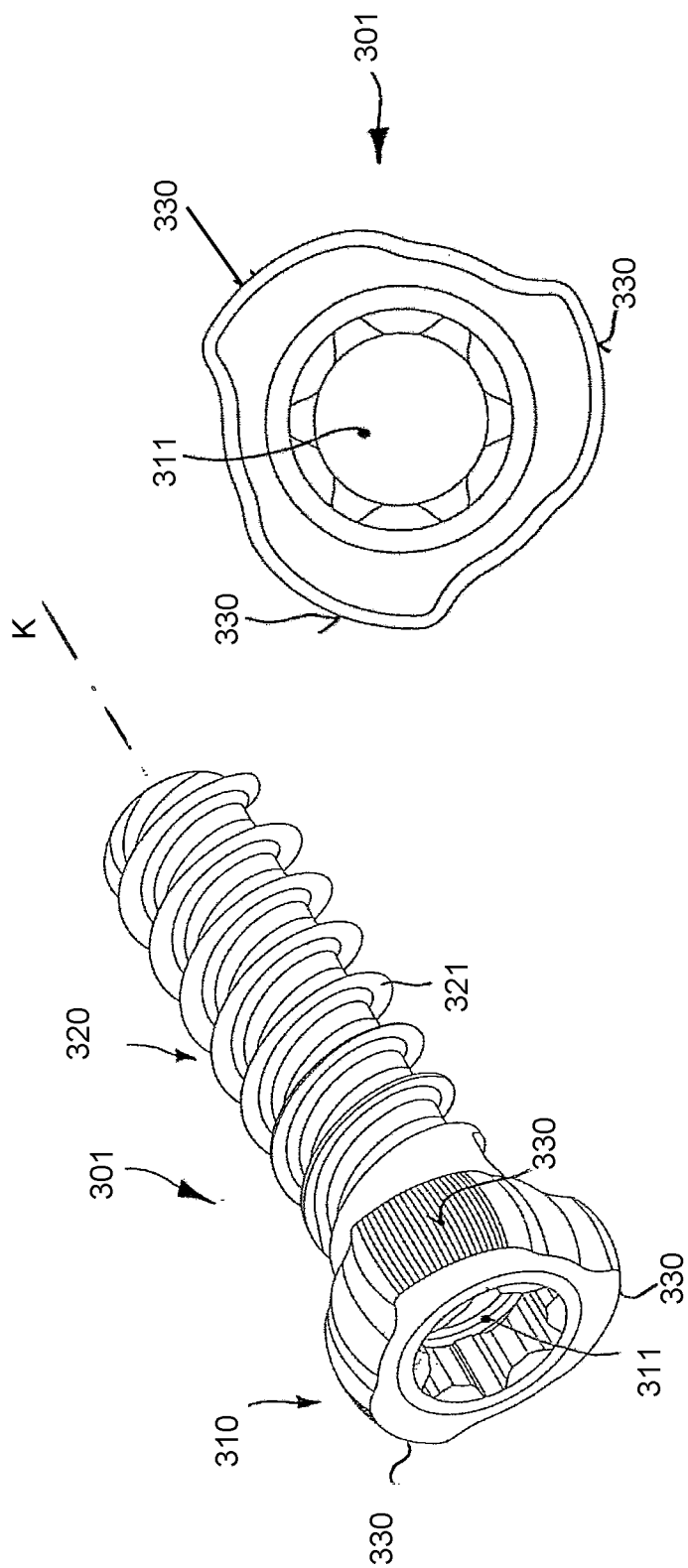

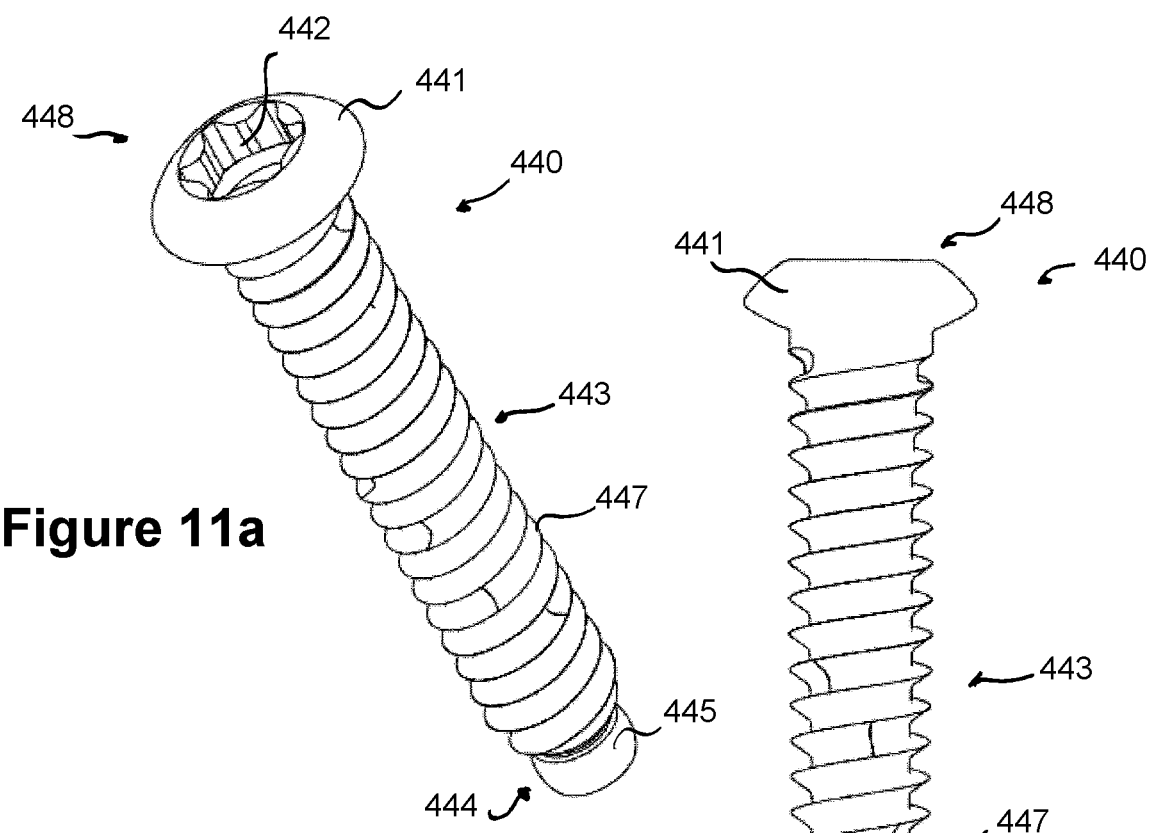
Figure 11a
Figure 11b
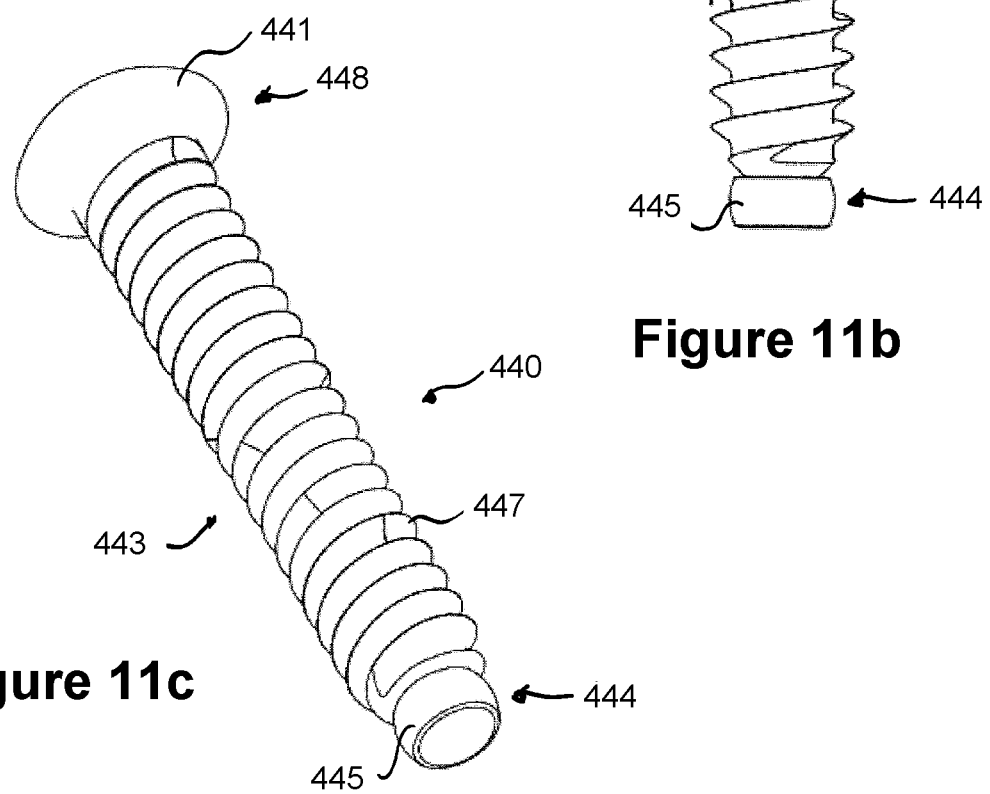
**Figure 11c

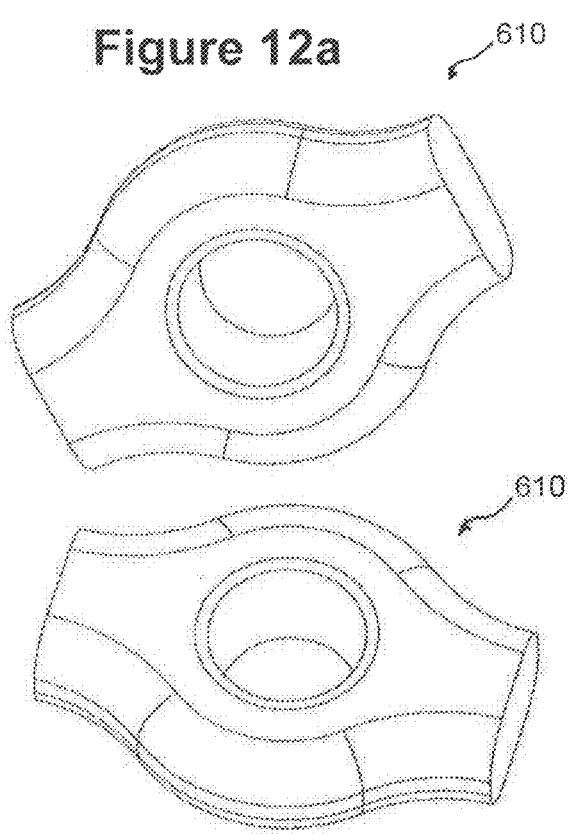
Figure 12a
Figure 12c
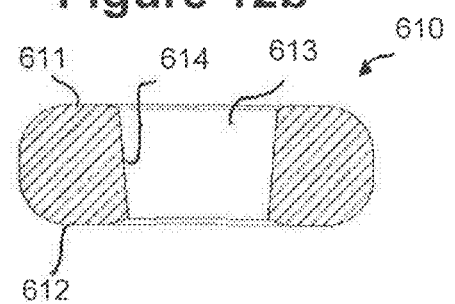
Figure 12b
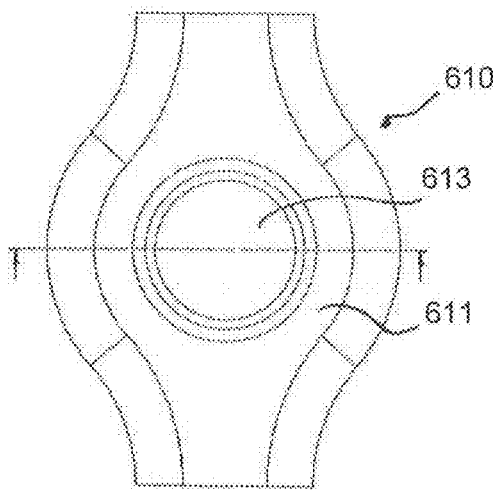
Figure 12d
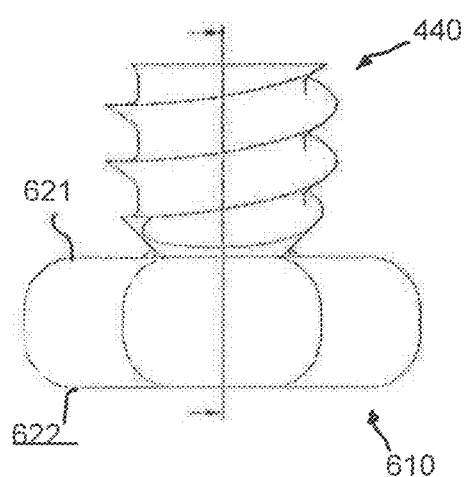
Figure 13a
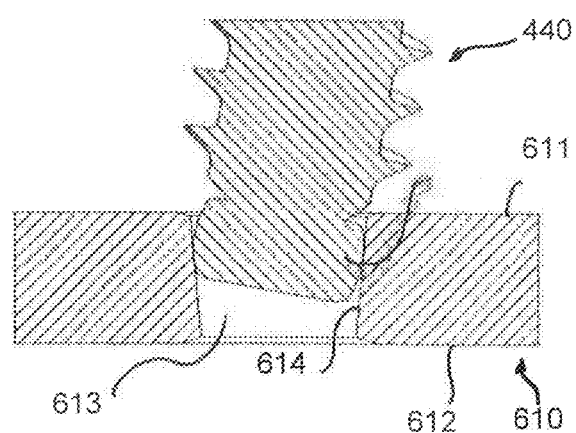
Figure 13b Figure 14a
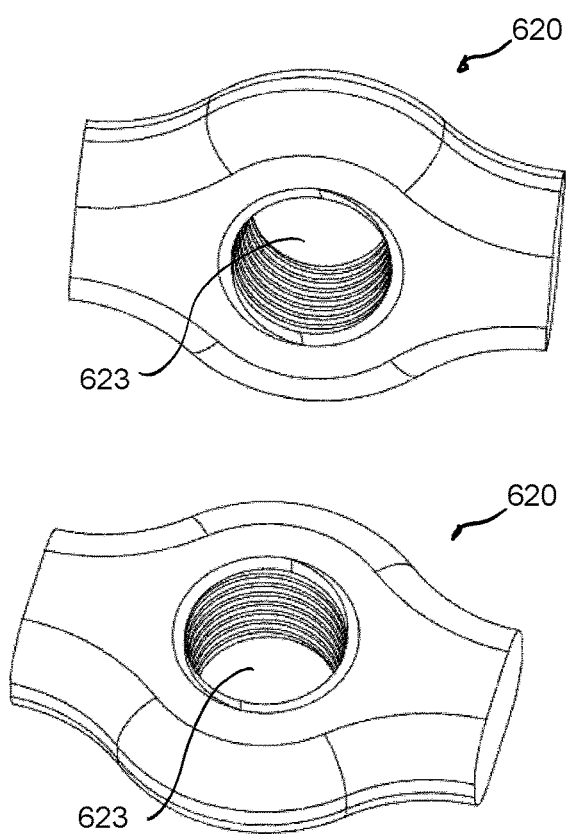
Figure 14c
Figure 14b
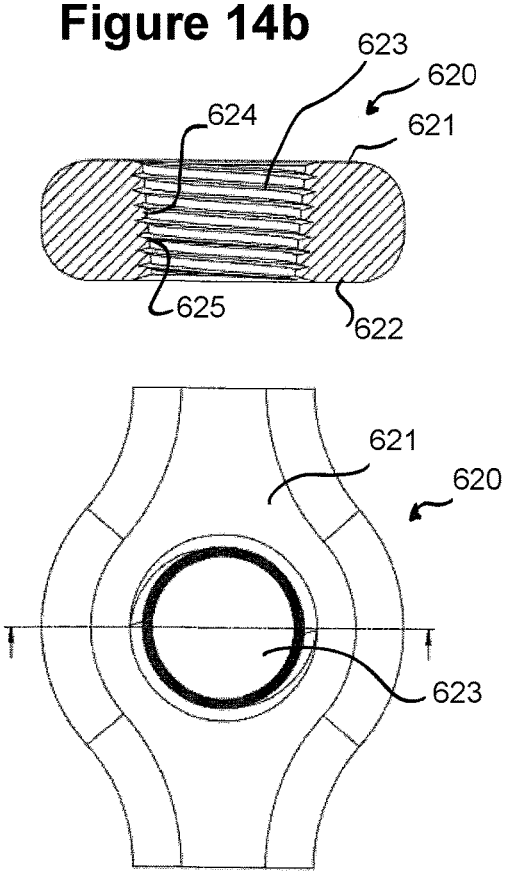
Figure 14d
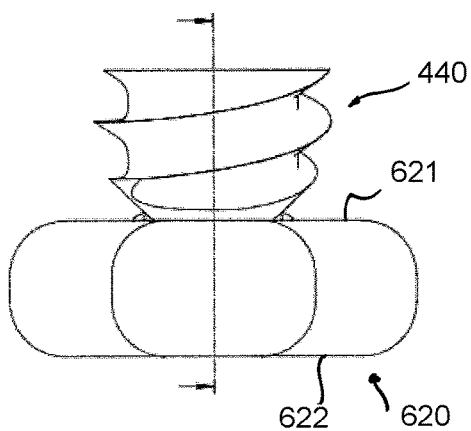
Figure 15a
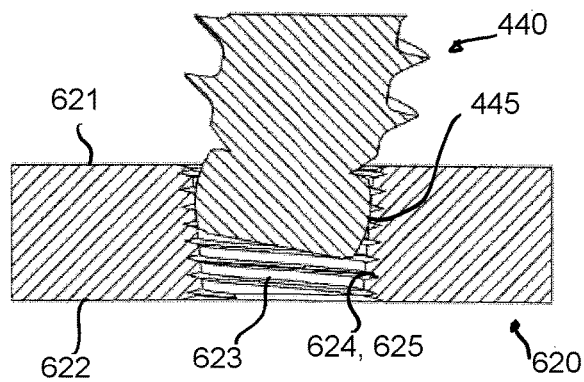
Figure 15b

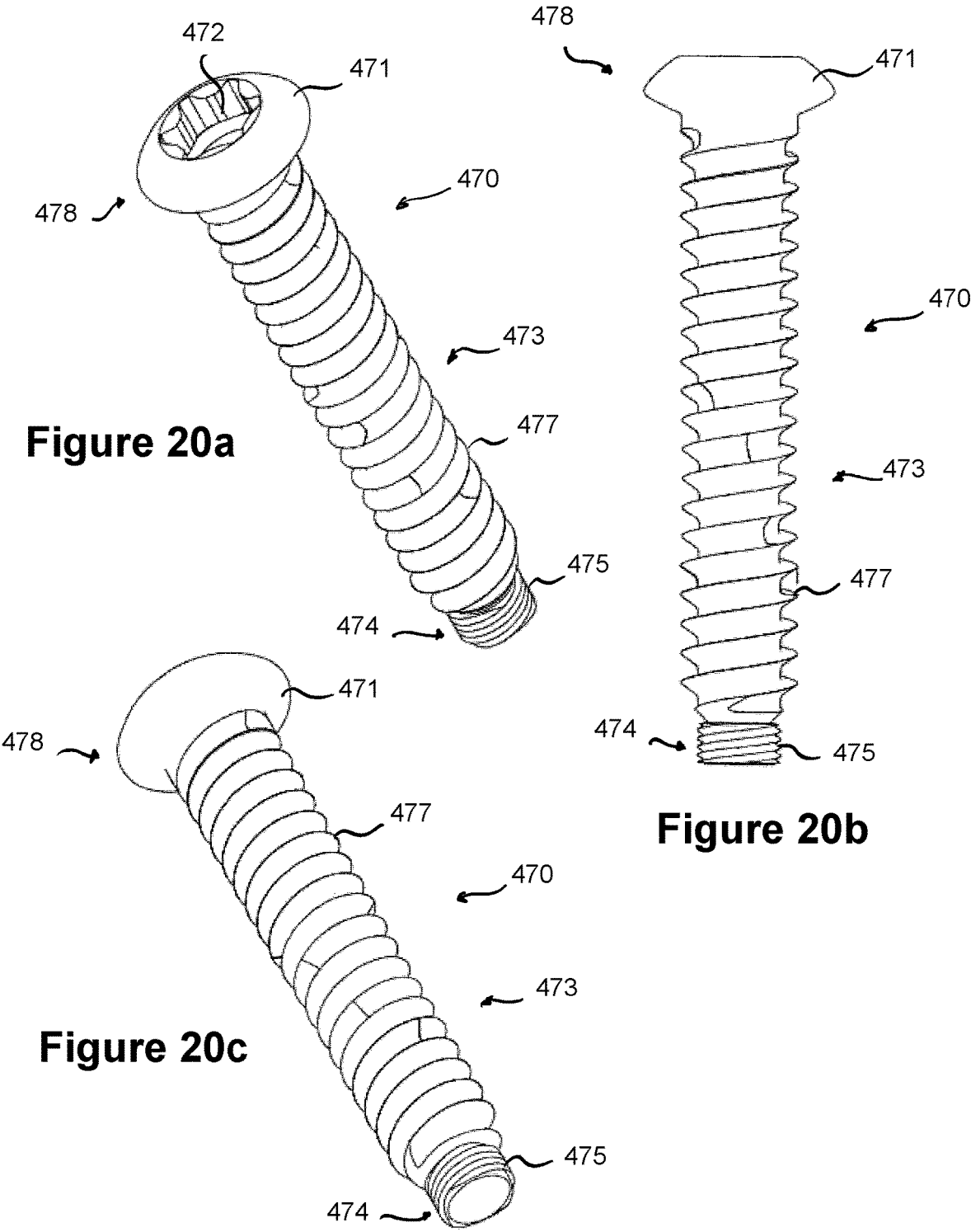

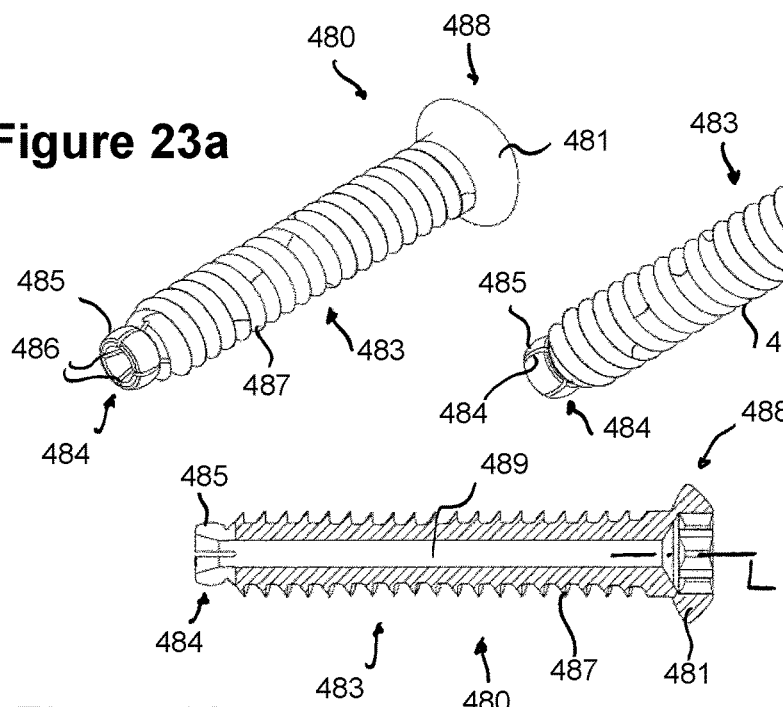
Figure 23a
Figure 23b
Figure 23c
Figure 23d
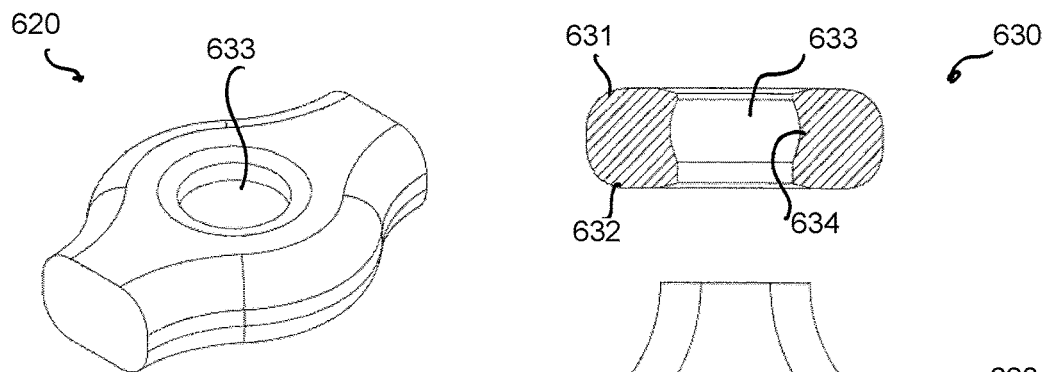
Figure 24a
Figure 24b
Figure 24c

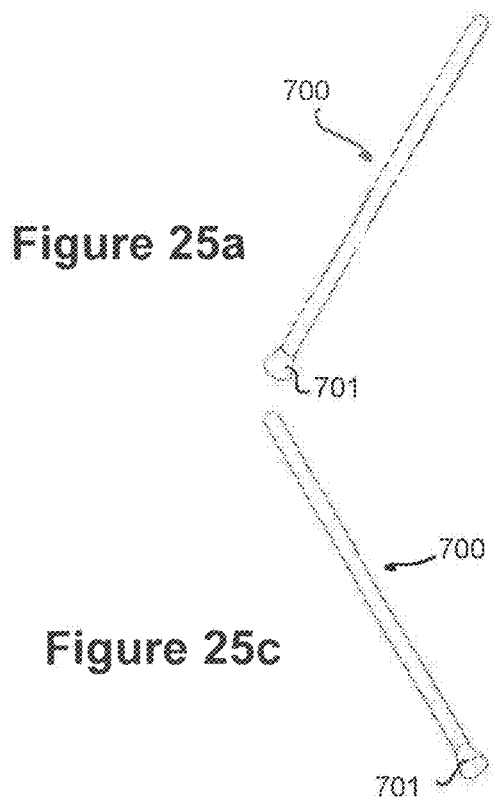
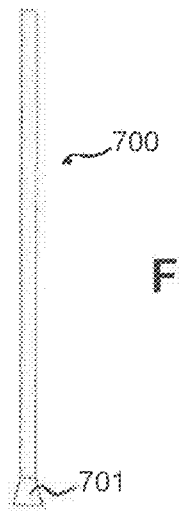
Figure 25a
Figure 25b
Figure 25c
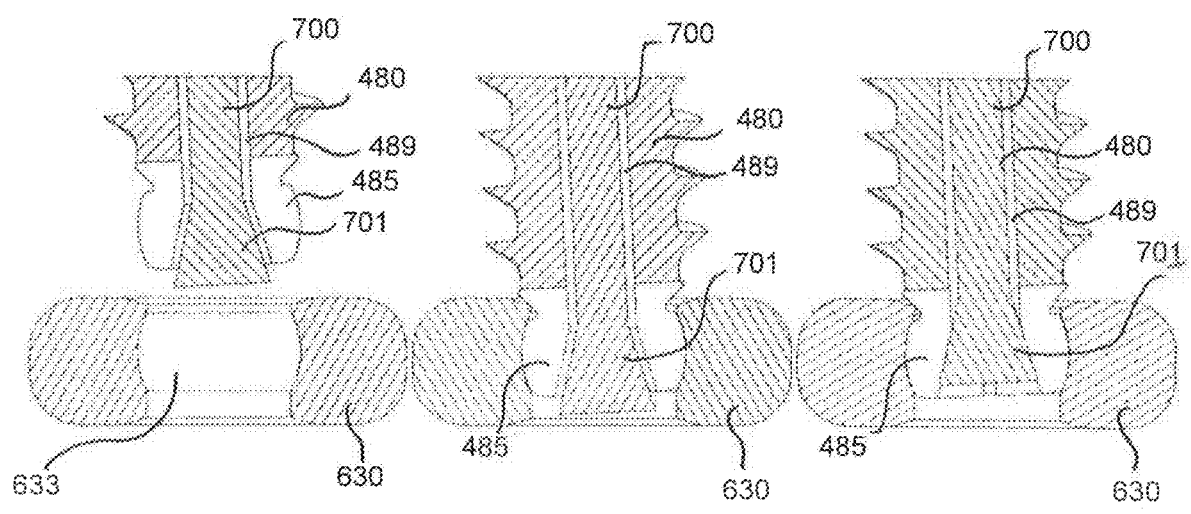
Figure 26a  Figure 26b  Figure 26c

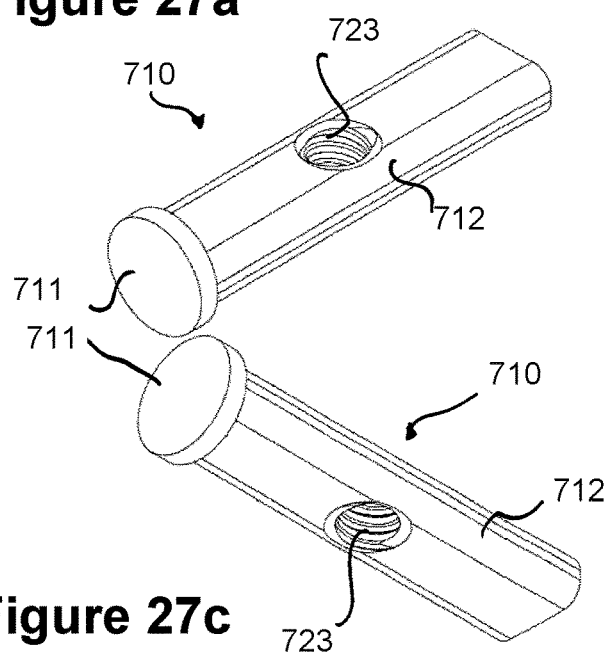
Figure 27a
Figure 27c
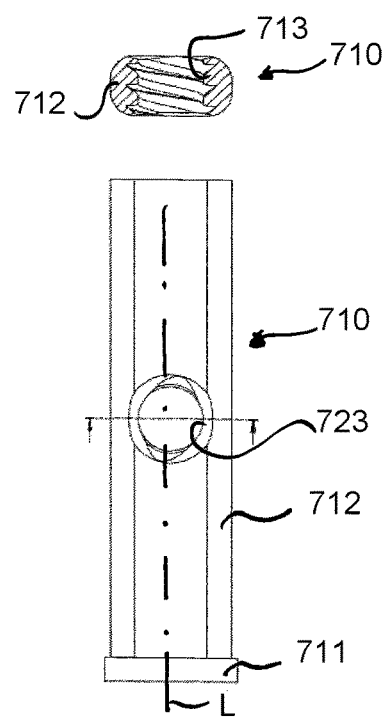
Figure 27b
Figure 27d
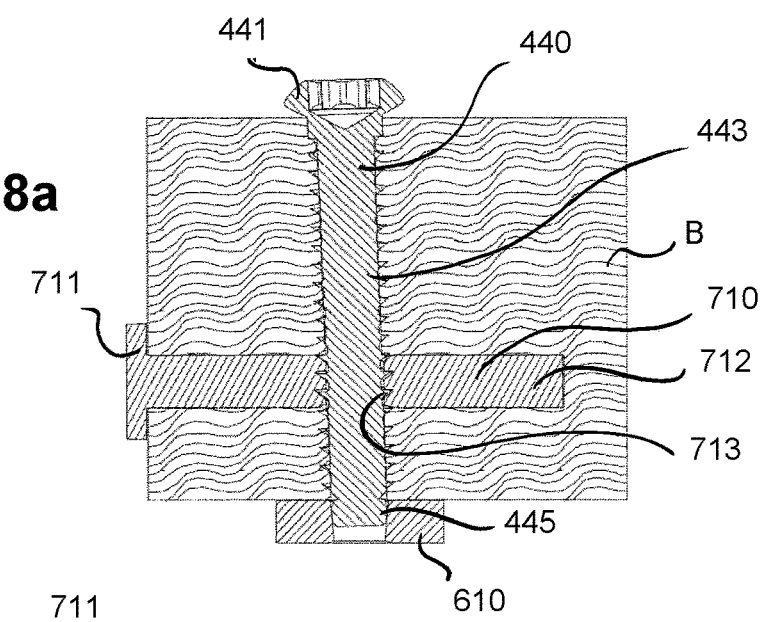
Figure 28a
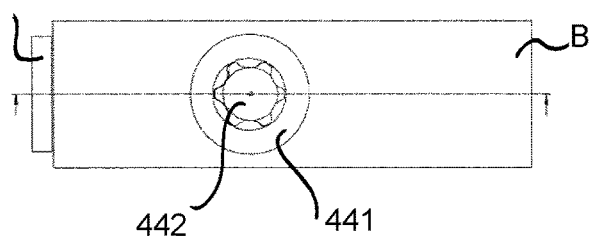
Figure 28b

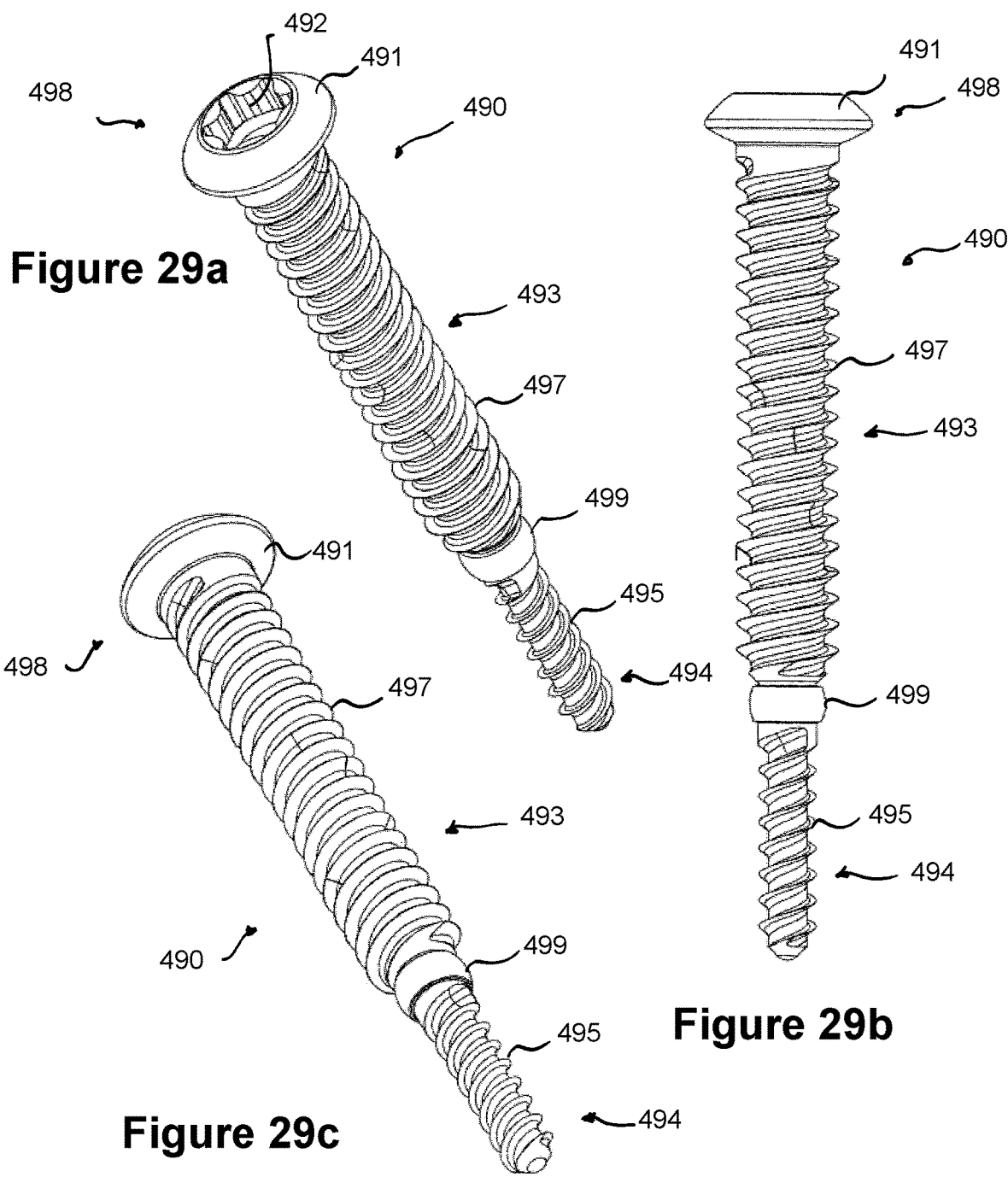

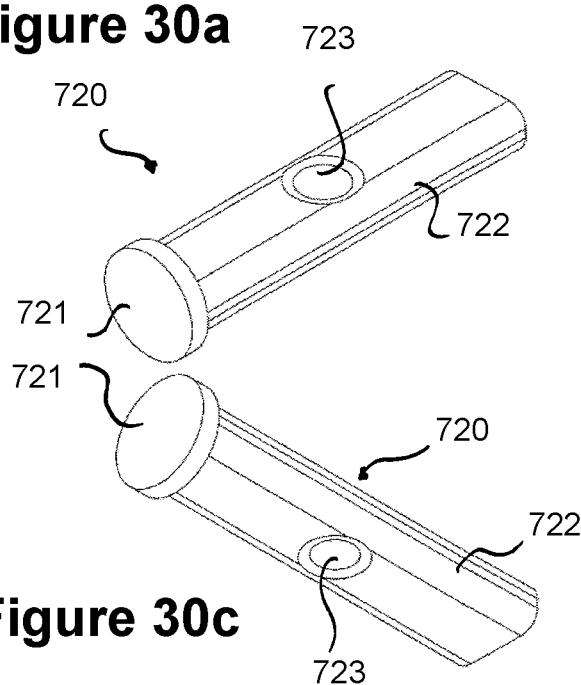
Figure 30a
Figure 30c
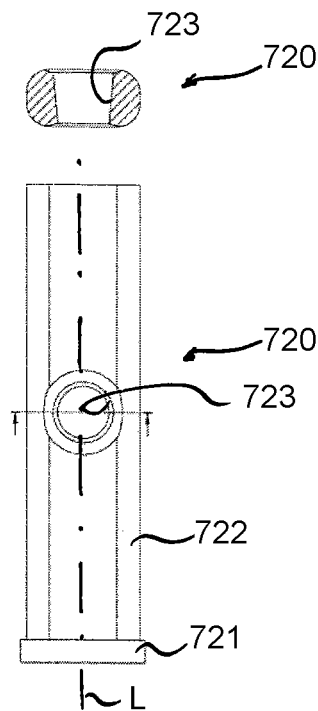
Figure 30b
Figure 30d
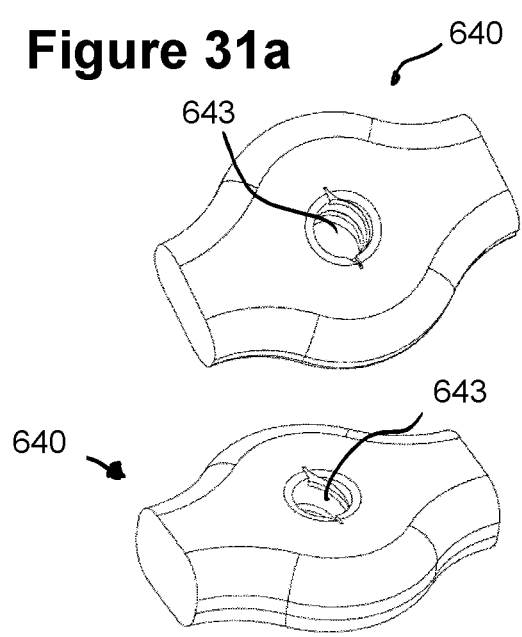
Figure 31a
Figure 31c
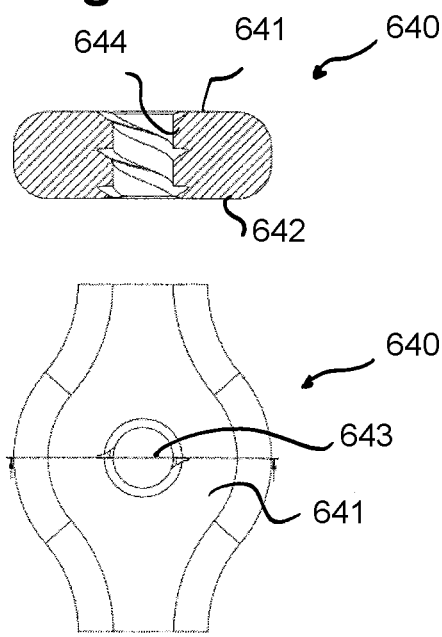
Figure 31b
Figure 31d

Figure 32a
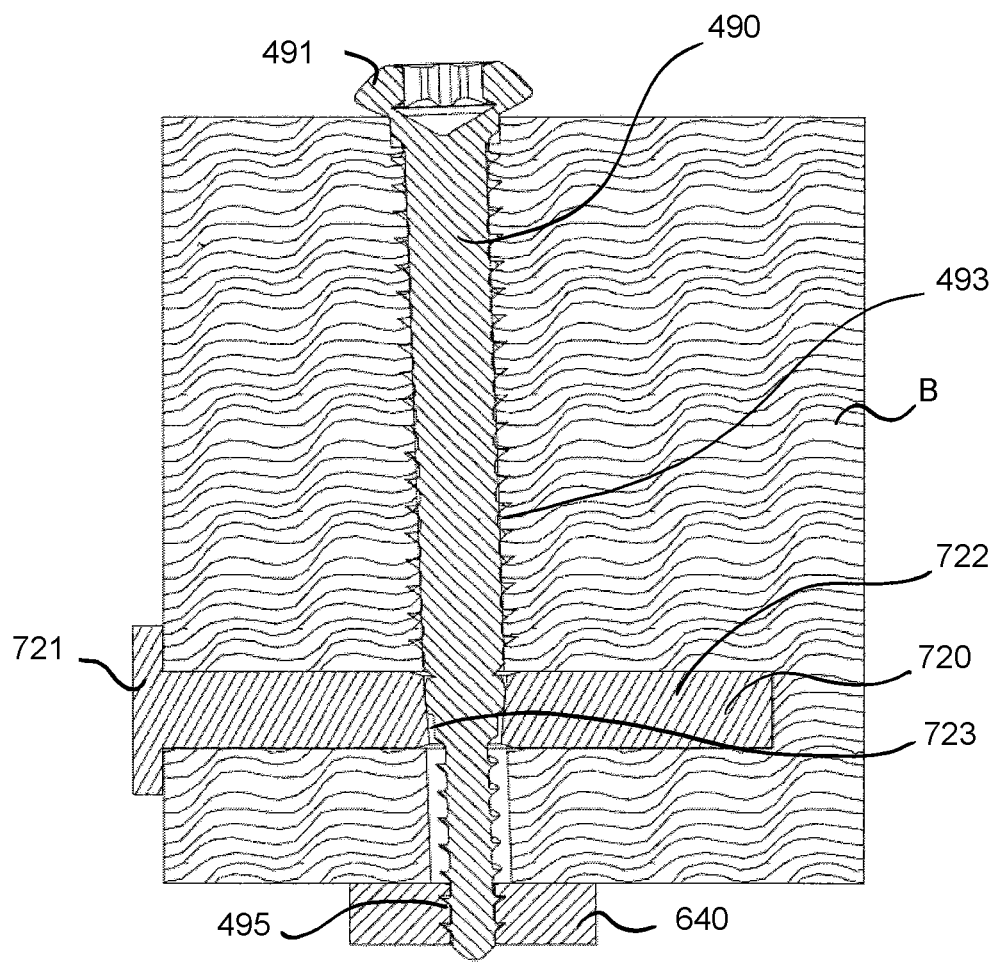
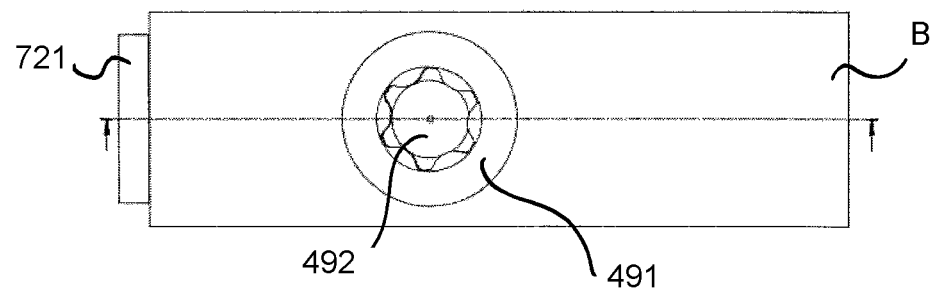
Figure 32b

Figure 33a
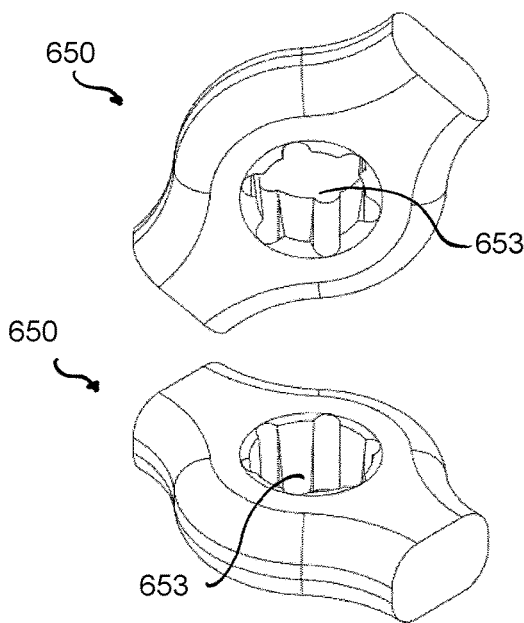
Figure 33b
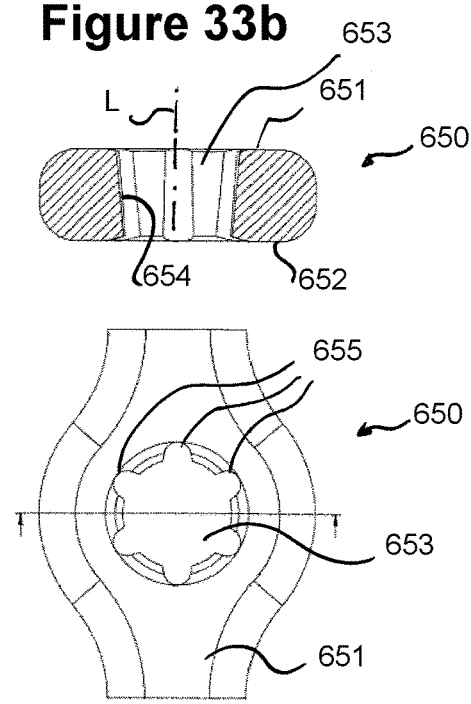
Figure 33c
Figure 33d
Figure 34a
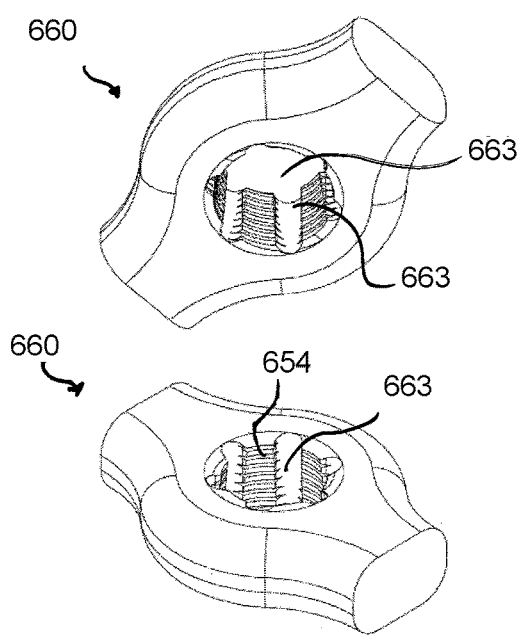
Figure 34b
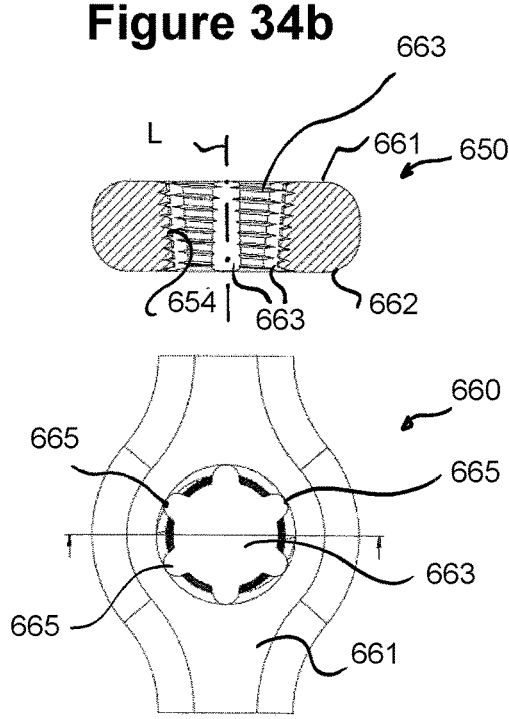
Figure 34c
Figure 34d

BONE SCREWS AND SURGICAL SETS COMPRISING BONE SCREWS

The present invention concerns bone screws and surgical sets comprising bone screws. More specifically, the invention relates to bone screws comprising a first end having an engagement contour, wherein the engagement contour is arranged for engagement with a tool for inserting or removing the bone screw, and a second end which is situated opposite the first end and on which a blocking element is arranged. In some embodiments, the blocking element may have an outer contour containing a cylindrical, spherical or conical portion, with or without a thread. Such a bone screw allows a connection with an opening of a bone plate at the bone screw's second end opposite the first end.

U.S. Pat. No. 9,125,700 B2 discloses a system and a method facilitating replacement of comminuted bone fractures or portions thereof adjacent bone joints. The system and method employ a prosthesis to replace at least a portion of the comminuted bone fractures. The prosthesis serves in reproducing the articular surface of the portion or portions of the comminuted bone fractures that are replaced. In doing so, the prosthesis serves in restoring joint viability and corresponding articulation thereof.

U.S. Pat. No. 8,911,482 B2 discloses an interlocking bone plate system. The system includes an outer bone plate for being arranged outside a broken bone, an inner bone plate for being installed inside the medullary cavity of the broken bone, and screws for being inserted through and engaged with the outer bone plate and the broken bone and then engaged with the inner bone plate so as to interlock the outer and inner bone plates together. The inner bone plate provides an added support in addition to the support provided by the outer bone plate, enhancing the structural strength of the whole bone fixation structure and lowering the risk of failed surgery.

US 2005/0234472 A1 discloses a method of directing a fastener to a bone plate, comprising: disposing a bone plate adjacent a bone; forming a guide path in a direction through the bone generally from an entry site adjacent the bone plate to an exit site spaced from the bone plate; and placing a fastener having a thread along the guide path opposite the direction such that the fastener approaches the bone plate from the bone and couples to the bone plate.

US 2009/0138051 A1 discloses an osteosynthesis implant. The implant has a plate-shaped base component having at least one hole, at least one axially extending rod-shaped tie rod having a first and a second end and at least one threaded component. The first end of the rod-shaped tie rod can be placed in the hole of the base component. The hole and the first end of the tie rod are formed such that the first end of the tie rod can be locked axially in the hole and is pivoted about an axis of the hole while locked to the plate. The second end of the tie rod is provided with a thread and the threaded component can be screwed onto the thread of the first tie rod. The tie rod can perform a pivoting movement of up to about 20° around the hole axis while locked in the plate hole.

DE 10 2010 048 052 A1 discloses a fixing device which is formed and arranged in the fixing holes such that it interacts with a locking screw. An endoprosthesis is provided, which is formed as a bone nail for internal fixation of bones, or as a combination of bone nail and bone plate, or as a shaft or pin.

DE 10 2014 107 495 A1 discloses a bone screw system comprising a bone screw having a shaft defining a longitudinal axis and a K-wire, which shaft has a longitudinal channel parallel to the longitudinal axis, comprising a shaft external thread, and a distal shank portion which is variable in its outer diameter, wherein the K-wire is configured to correspond or substantially correspond to the longitudinal channel, characterized by an expansion element cooperating with the distal shaft section and arranged at the K-wire, for expanding the shank portion.

Furthermore, in some situations, the presence and location of soft tissue prevents a placement of a bone screw through the bone plate and then into the bone from above. There is a need to provide systems which can also be used in such situations.

A first aspect of the present invention relates to a bone screw as such. The bone screw comprises a first end having an engagement contour which is arranged for engagement with a tool for inserting or removing the bone screw. For example, the tool may be a screwdriver which can be inserted in order to insert or remove the bone screw. The bone screw further comprises a second end which is situated opposite the first end and on which a blocking element is arranged.

Such bone screws according to the invention can be applied also in some situations explained above in which soft tissue has to be protected. In these situations, the bone plate can be placed below the soft tissue from the side, and the bone screw can be inserted through the bone and then into the bone plate from below.

In one aspect, the blocking element is provided with a circumferential outside surface which comprises at least one clamping surface which—when viewed in an azimuth plane perpendicular to a longitudinal axis of the bone screw—widens outwardly in a wedge-shaped manner away from the longitudinal axis, as disclosed in WO 2004/086990, for example. The outside surface may extend substantially in the direction of a longitudinal axis of the bone screw.

The bone screw may comprise a screw head which is arranged at the first end of the bone screw and contain the engagement contour. The screw head may have a spherical head underside. The bone screw may comprise a screw shank extending between the first end and the second end and contain a thread, in particular a bone thread, wherein the screw head protrudes outwardly above a screw shank and the thread.

Preferably, the blocking element is designed such that the bone screw can be received in a receiving opening of a bone plate and fixed to the bone plate at different angles relative to the bone plate. Also with preference, the blocking element is designed such that the bone screw can be fixed in the receiving opening by rotating the bone screw.

In some embodiments, the circumferential outside surface is realized in an at least approximately spherical, paraboloid, ellipsoid or hyperboloid manner at least in the region of the clamping surface.

In some embodiments, the blocking element includes at least one, preferably at least two, more preferably at least three or even precisely three clamping surfaces which are preferably distributed at least substantially uniformly in the circumferential direction.

The bone screw may contain a cannula extending along a longitudinal axis of the bone screw. A K-wire may be at least partially received in this cannula in order to direct the bone screw to a desired site and/or in a desired orientation with respect to a bone and/or a bone plate.

In addition to the blocking element which is arranged on the second end of the bone screw, the bone screw may contain a further blocking element which is arranged between the first end and the second end of the bone screw.

This further blocking element allows to further fix the bone screw, for example in interaction with a bone nail.

The invention also pertains to a surgical set including at least one bone screw as disclosed above and at least one bone plate including at least one opening which is at least partially delimited by an inside wall having an inner contour for receiving and fixing the blocking element of the bone screw, i.e. the blocking element arranged at the second end of the bone screw. The opening may penetrate the bone plate along a longitudinal axis from a first surface of the bone plate to an oppositely situated second surface of the bone plate.

Another aspect of the invention relates to a surgical set including at least one bone screw and at least one bone plate. The bone screw comprises a first end having an engagement contour which is arranged for engagement with a tool for inserting or removing the bone screw. The bone screw further contains a second end which is situated opposite the first end and on which a blocking element is arranged, wherein the blocking element is provided with a circumferential outside surface having an outer contour. The bone plate includes at least one opening which is at least partially delimited by an inside wall having an inner contour for receiving and fixing the blocking element of the bone screw, i.e. the blocking element arranged at the second end of the bone screw. The opening may penetrate the bone plate along a longitudinal axis from a first surface to an oppositely situated second surface.

In this aspect of the invention, the outer contour is substantially different from the inner contour. Within the present invention, the outer contour is regarded as substantially different from the inner contour when, for example,

- the outer contour contains at least one portion which is essentially spherical, but the inner contour does not contain at least one portion which is essentially spherical; and/or
- the inner contour contains at least one portion which is essentially spherical, but the outer contour does not contain at least one portion which is essentially spherical; and/or
- the outer contour contains at least one portion which is essentially cylindrical, but the inner contour does not contain at least one portion which is essentially cylindrical; and/or
- the inner contour contains at least one portion which is essentially cylindrical, but the outer contour does not contain at least one portion which is essentially cylindrical; and/or
- the outer contour contains at least one portion which is essentially conical, but the inner contour does not contain at least one portion which is essentially conical; and/or
- the inner contour contains at least one portion which is essentially conical, but the outer contour does not contain at least one portion which is essentially conical.

These embodiments may have the advantage that they can be manufactured rather easily and at relatively small costs.

The terms "essentially spherical", "essentially conical" and "essentially cylindrical", when used for a contour in the present application, all encompass the possibility that the contour also contains a thread. In particular, a bone screw may contain a thread in the form of a bone thread. Moreover, these terms also encompass the possibility that the spherical, conical or cylindrical contour is interrupted by at least one indentation that extends in a radial direction with respect to a longitudinal axis of the bone screw or of the opening of the bone plate.

The outer contour may contain at least one first portion which is essentially spherical and has a first radius and at least one second portion which is essentially spherical and has a second radius which is different from the first radius.

Yet another aspect of the invention relates to a surgical set including at least one bone screw and at least one bone plate. The bone screw comprises a first end having an engagement contour for engagement which is arranged for engagement with a tool for inserting or removing the bone screw. The bone screw further comprises a second end which is situated opposite the first end and on which a blocking element is arranged, wherein the blocking element is provided with a circumferential outside surface having an outer contour. The bone plate includes at least one opening which is at least partially delimited by an inside wall having an inner contour for receiving and fixing the blocking element of the bone screw. As above, the opening may penetrate the bone plate along a longitudinal axis from a first surface to an oppositely situated second surface. In this aspect of the invention, the outer contour and the inner contour are both essentially spherical with similar or equal radii.

The bone screw of the surgical set may contain a cannula extending along a longitudinal axis of the bone screw. A K-wire may be at least partially received in this cannula in order to direct the bone screw to a desired site and/or in a desired orientation with respect to a bone and/or a bone plate. The blocking element may be hollow and surround an inner end portion of the cannula which widens towards a mouth of the cannula. For example, the inner end portion of the cannula may be conical or contain at least one step. The blocking element may contain at least one slot which substantially extends in a longitudinal direction of the bone screw. Due to the at least one slot, the blocking element may be expanded and thereby fixed to an opening of a bone plate.

Accordingly, the surgical set may further contain at least one K-wire which is dimensioned such that it can be at least partially received in the cannula. The K-wire may contain a tip which widens towards its end, in particular a conical tip, dimensioned such that a contact between the widening tip of the K-wire and the widening inner end portion of the cannula causes an expansion of the blocking element when the K-wire is pulled along the longitudinal direction of the bone screw. Due to this expansion, the blocking element can be fixed in an opening of a bone plate.

Alternatively, the hollow blocking element may surround an inner end portion of the cannula which narrows towards a mouth of the cannula. The surgical set may then further contain at least one K-wire having a cylindrical tip dimensioned such that a contact between the cylindrical tip and the conical inner end portion of the cannula causes an expansion of the blocking element when the K-wire is pushed along the longitudinal direction of the bone screw. Due to this expansion as well, the blocking element can be fixed in an opening of a bone plate.

In addition to the blocking element which is arranged on the second end of the bone screw, the bone screw may contain a further blocking element which is arranged between the first end and the second end of the bone screw. This further blocking element allows to further fix the bone screw, for example in interaction with a bone nail.

In many situations, it is advantageous when a bone screw, through corresponding design of both a blocking element of the bone screw, in particular of the screw head, and of the plate opening, can be fixed at different angles relative to a bone plate. These types of structures at screw heads and plate openings are disclosed, for example, in international patent application WO 2004/086990. The plate openings disclosed there, however, only allow the blocking element, in particular the screw head, to be fixed at a variable angle when the screw is inserted through the openings from a predefined first surface of the bone plate in the direction of a predefined oppositely situated second surface of the bone plate; variable angle fixing in a direction opposite to this is not possible. This can restrict the usefulness of the bone plate for many applications.

Specific embodiments of the present invention are directed to surgical sets comprising bone plates and bone screws which can be fixed in the bone plate at a variable angle in both directions.

This and further objects are achieved by any of the surgical systems as described above, wherein the bone plate contains at least one opening for receiving in each case at least one bone screw. For example, this can be a bone plate for the reconstruction or trauma treatment of an in particular human bone, such as, for instance, an in particular human foot or mandible.

The opening may penetrate the bone plate along a longitudinal axis from a first surface of the bone plate to an oppositely situated second surface of the bone plate. On the first surface, the opening may open out into a first receiving region which is realized for the receiving and in particular angularly-variable fixing of a blocking element of a bone screw in a first direction.

In specific embodiments of the present invention, on the second surface, the opening opens out into a second receiving region which is realized for the receiving and in particular angularly-variable fixing of the blocking element in a second direction. In this case, the second direction is substantially opposite the first direction. This means, here and below, that the blocking element can be received and fixed in the first receiving region in such a manner that the bone screw passes through the bone plate from the first surface in the direction of the second surface, and the blocking element can be received and fixed in the second receiving region in such a manner that the bone screw passes through the bone plate from the second surface in the direction of the first surface.

In a preferred manner, the first receiving region is delimited by a first inside wall and the second receiving region is delimited by a second inside wall, wherein in each case at least one recess is formed both in the first inside wall and in the second inside wall and in each of said recesses the distance away from the respective inside wall increases in dependence on the angle of rotation about the longitudinal axis. In an even more preferred manner, both the first inside wall and the second inside wall are realized in an at least approximately spherical, paraboloid, ellipsoid or hyperboloid manner in the region of each of the respective recesses.

In other words, the opening therefore includes, in a preferred manner, an inside wall both in the region of the first surface of the bone plate and in the region of the second surface of the bone plate, said inside wall being provided in each case as disclosed in WO 2004/086990.

The first and the second receiving regions of the opening can be realized independently of one another for right-rotating blocking or for left-rotating blocking. In this case, right-rotating blocking, for example, for the first receiving region means that the blocking element of the bone screw, when viewed in a viewing direction from the first surface of the bone plate to the second surface of the bone plate, is fixable in the first receiving region as a result of rotating the bone screw clockwise. In an analogous manner, left-rotating blocking, for example, for the second receiving region, means that the blocking element, when viewed in a viewing direction from the first surface of the bone plate to the second surface of the bone plate, is fixable in the first receiving region as a result of rotating the bone screw anticlockwise.

In a preferred manner, the first and the second receiving regions of the opening are realized for same-direction blocking. This means that either both receiving regions are realized for right-rotating blocking or both receiving regions are realized for left-rotating blocking.

Said design allows a correspondingly designed bone screw to be both inserted though the opening from the first surface in the direction of the second surface and fixed at a variable angle in this manner and to be inserted through the opening from the second surface in the direction of the first surface and to be fixed at a variable angle in this manner. This makes it possible to design bone plates in such a manner that either the second surface or the first surface can be contacted onto the bone. This is particularly useful when the presence and location of soft tissue prevents a placement of a bone screw through the bone plate and then into the bone from above. The bone screw may then simply be placed through the bone and then into the bone plate from below.

Moreover, one and the same bone plate can be used either for a left-sided or for a right-sided defect. In this manner, even fewer different bone plates are necessary in order to allow for individual adaptation, which simplifies storage even more.

The bone plate even allows for some applications where at least one first bone screw can be inserted through a first opening from the first surface in the direction of the second surface and at least one second bone screw can be inserted through a second opening from the second surface in the direction of the first surface in one and the same bone plate and can be fixed at a variable angle.

The first and/or the second inside wall can comprise, independently of one another, one, several or all the features disclosed in WO 2004/086990. The disclosure in this respect in WO 2004/086990 is hereby expressly incorporated into the present application.

In particular, the inside wall can comprise at least one, preferably at least two, more preferably at least three or even precisely three recesses which are preferably distributed at least substantially uniformly along its circumference and widen outwardly in each case in a wedge-shaped manner away from the longitudinal axis of the receiving means; and/or the receiving region can be provided with an in particular spherical depression for receiving, for example, a screw head with a spherical head underside.

As previously explained, the invention encompasses surgical sets which include at least one bone plate as described above having at least one opening with two receiving regions as well as at least one bone screw with a screw shank and a blocking element, in particular a screw head which protrudes outwardly above the screw shank and a thread, in particular a bone thread, of the screw shank. In this case, the blocking element is receivable electively in the first receiving region or in the second receiving region of the opening of the bone plate and is fixable in particular at a variable angle.

In a preferred manner, the blocking element, in particular the screw head, is provided with a circumferential outside surface which extends substantially in the direction of a longitudinal axis of the bone screw and comprises at least one clamping surface which—when viewed in an azimuth plane perpendicular to the longitudinal axis—widens outwardly in a wedge-shaped manner away from the longitudinal axis. In a preferred manner, the circumferential outside surface of the blocking element is realized in an at least approximately spherical, paraboloid, ellipsoid or hyperboloid manner at least in the region of the clamping surface.

In other words, the bone screw is realized in a preferred manner in the manner in which it is disclosed in WO 2004/086990.

A bone screw designed in such a manner allows for elective insertion into the opening of the bone plate in directions which are substantially opposite one another, as has already been explained above. The bone screw can also comprise one, several or all of the features disclosed in WO 2004/086990; the disclosure in this respect in WO 2004/086990 is also hereby expressly incorporated into the present application. In particular, the outside surface can comprise at least three or even precisely three clamping surfaces which are distributed at least substantially uniformly along its circumference and widen outwardly in each case in a wedge-shaped manner away from the longitudinal axis. The outside surface may also comprise only one or two such clamping surfaces.

Figure 35A:
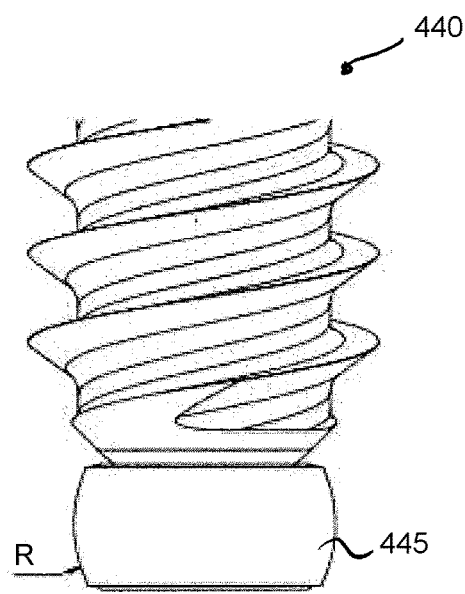
Figure 35B:
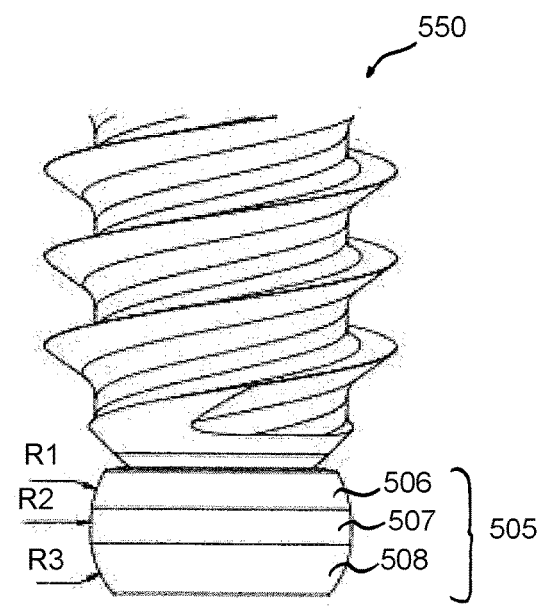
Figure 3A:
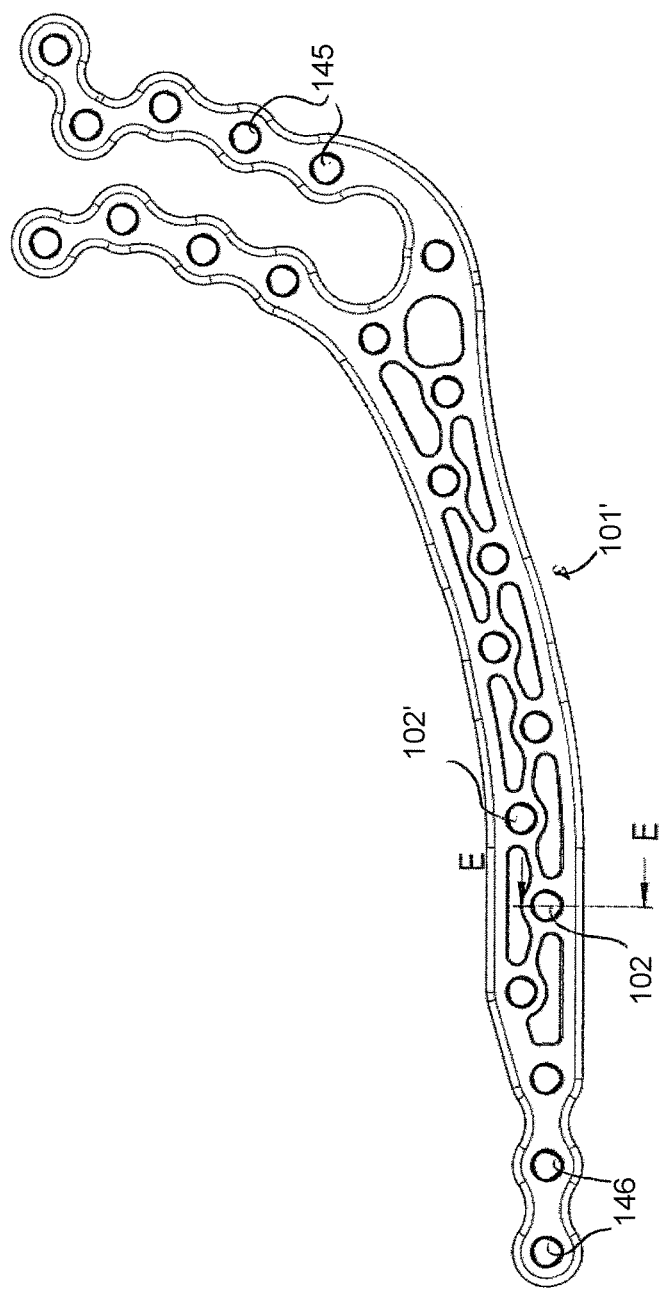
Figure 3B:
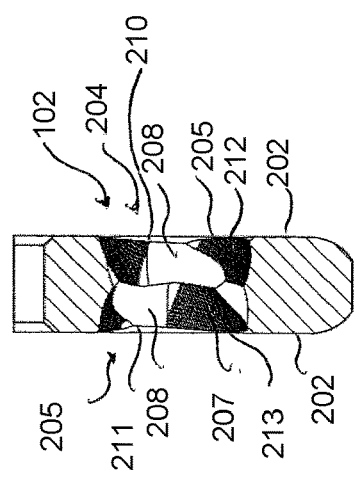
Figure 5A:
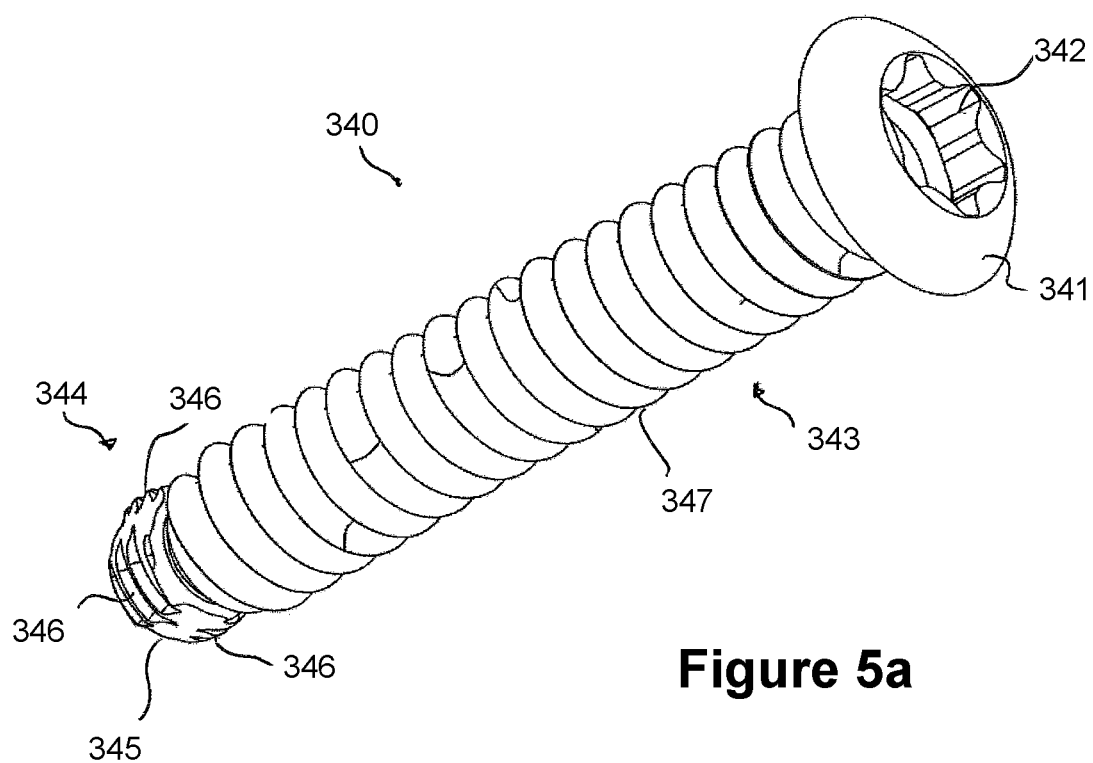
Figure 6A:
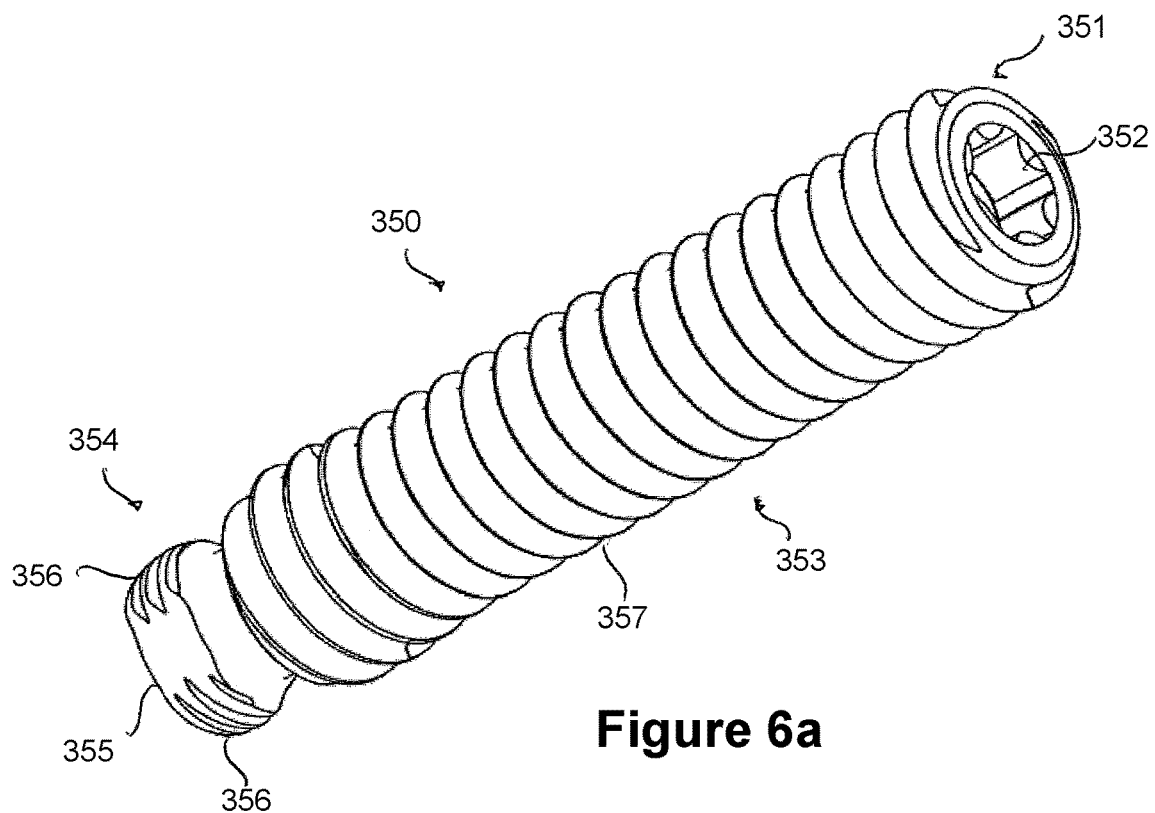
Figure 7A:
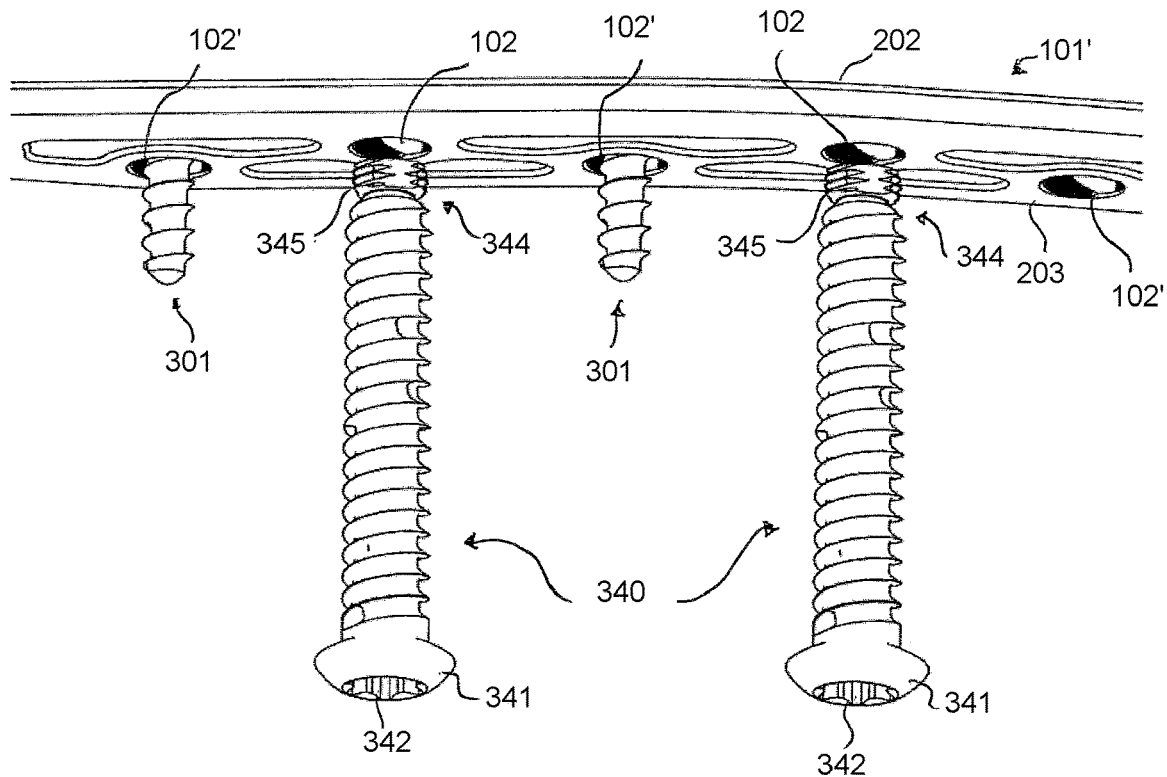
Figure 7B:
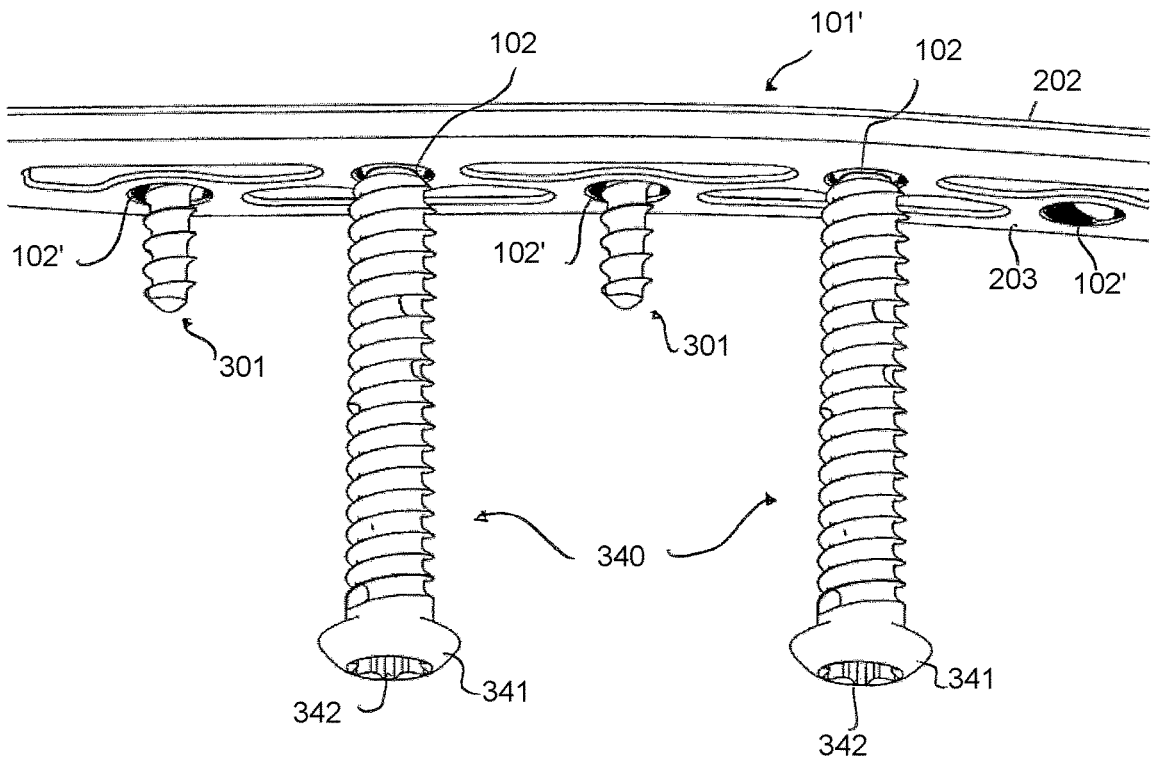
Figure 7C:
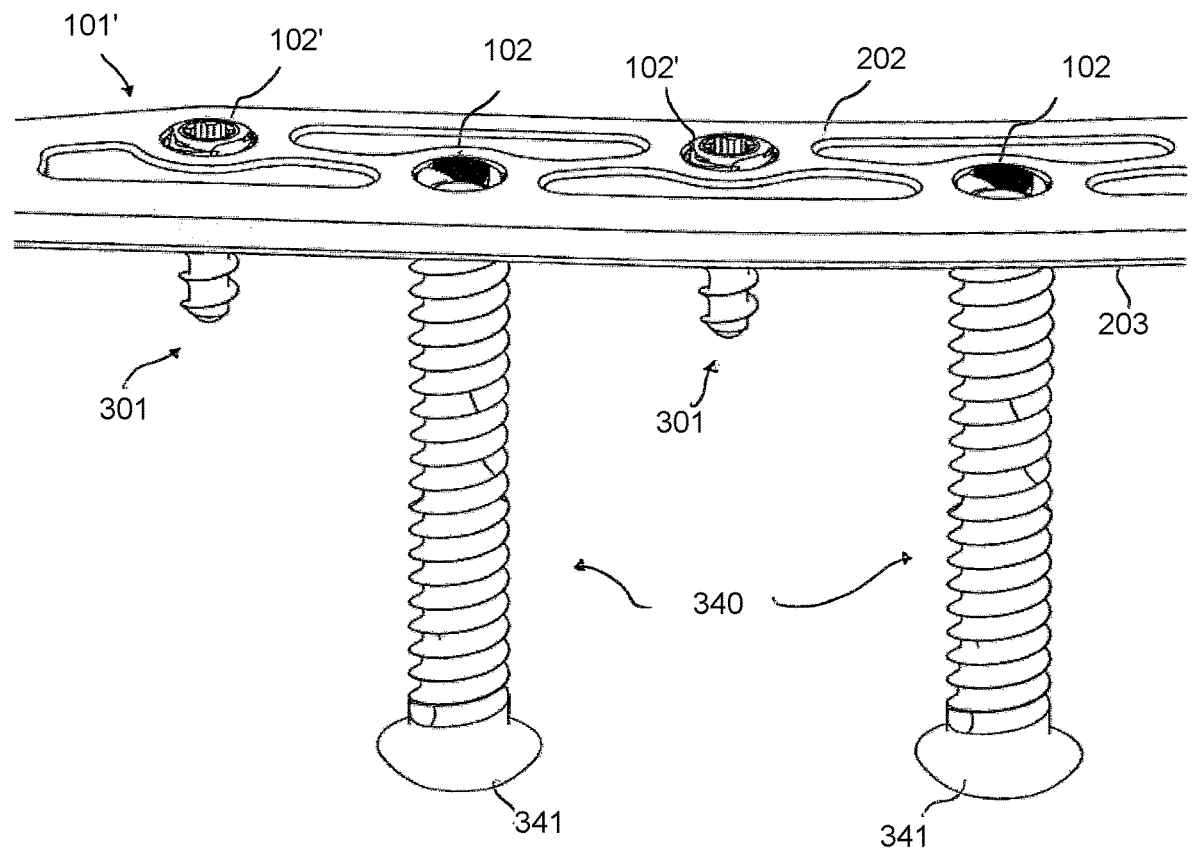
Figure 8A:
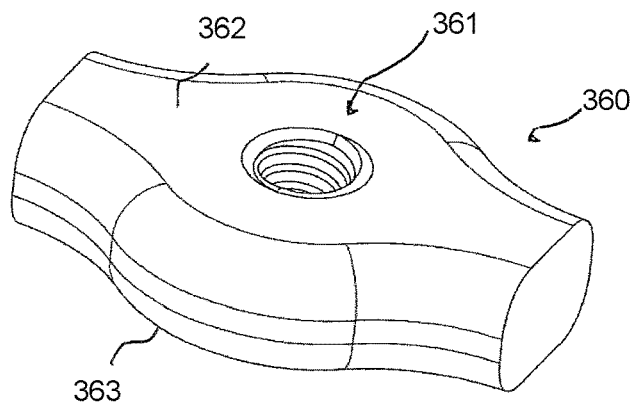
Figure 8B:
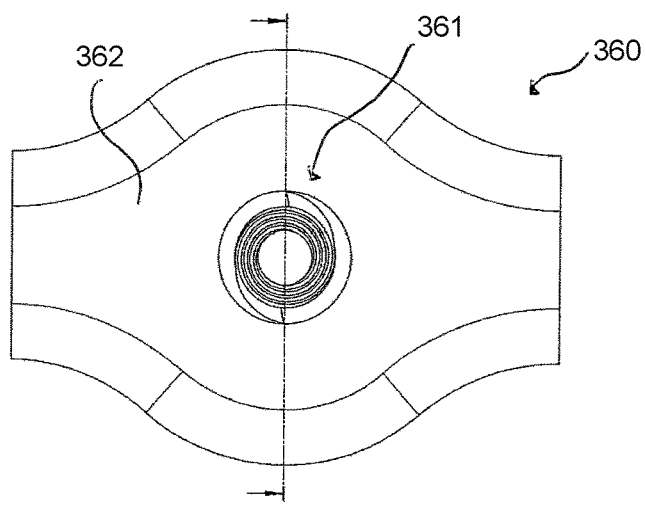
Figure 8C:
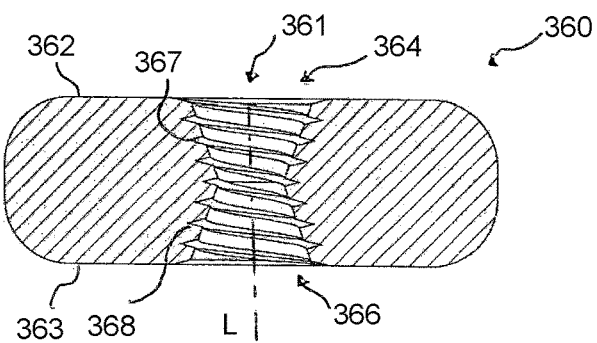
Figure 9A:
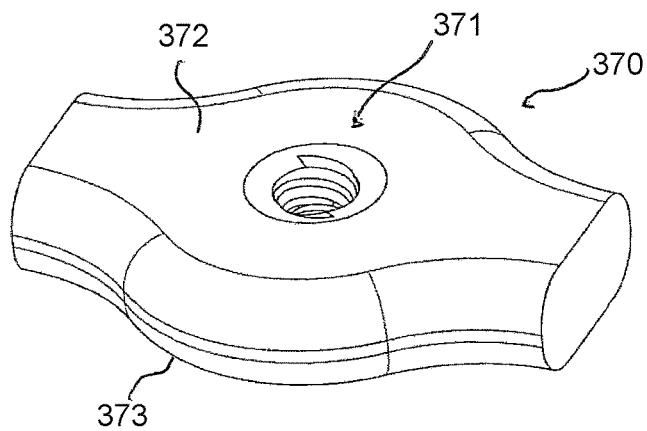
Figure 9B:
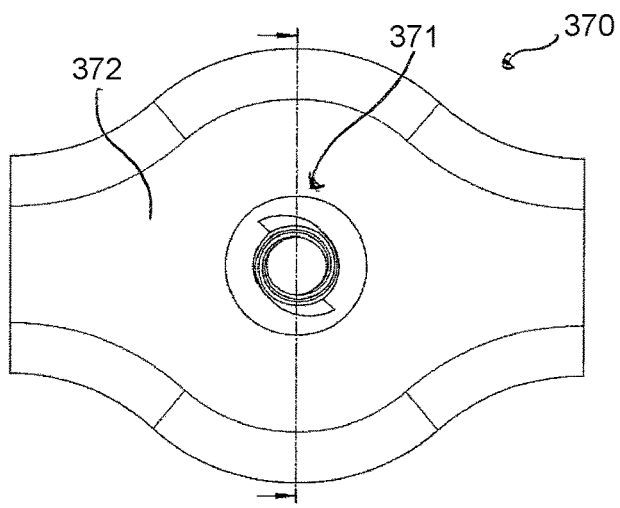
Figure 9C:
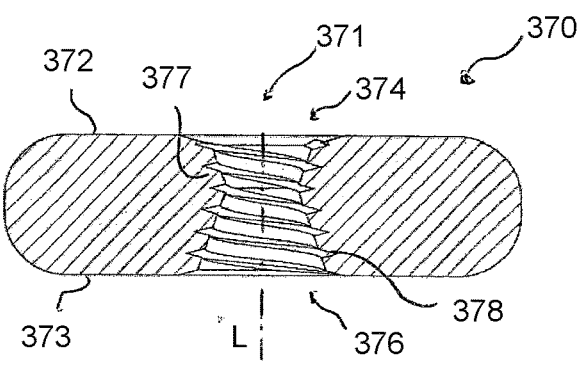
Figure 10A:
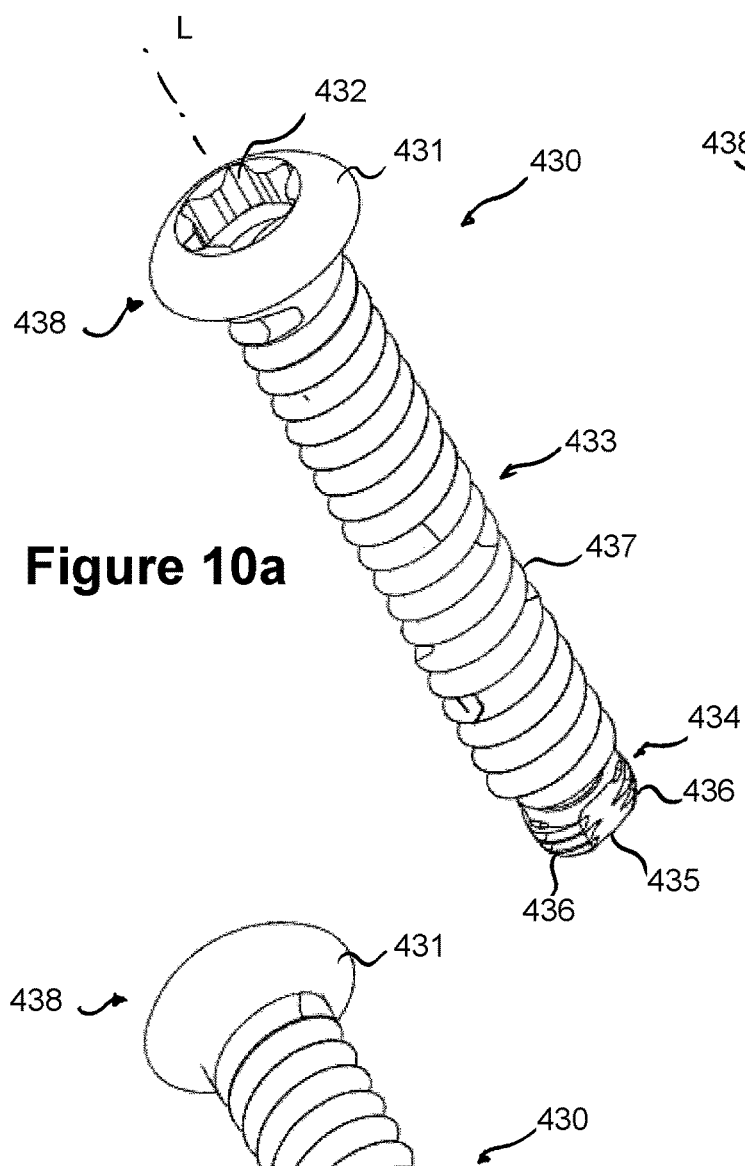
Figure 10B:
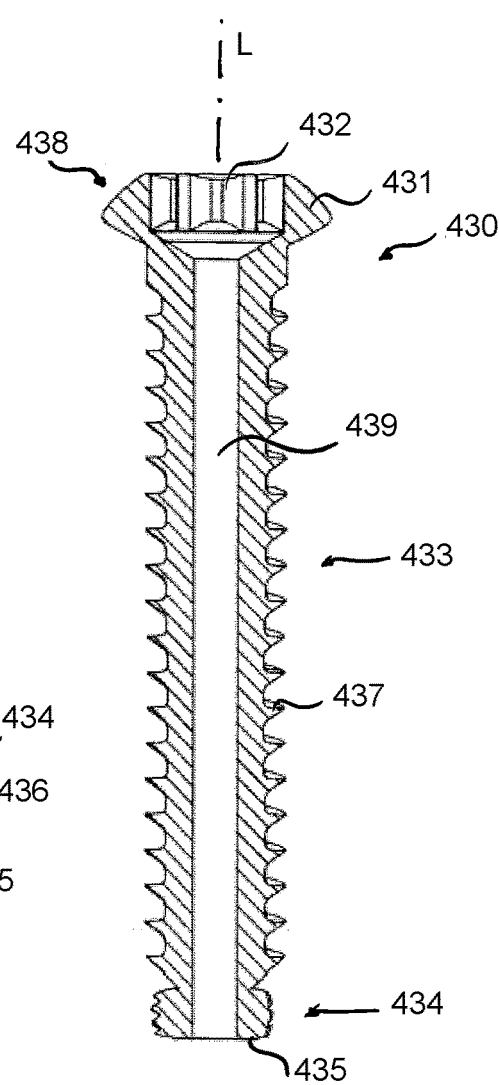
Figure 10C:
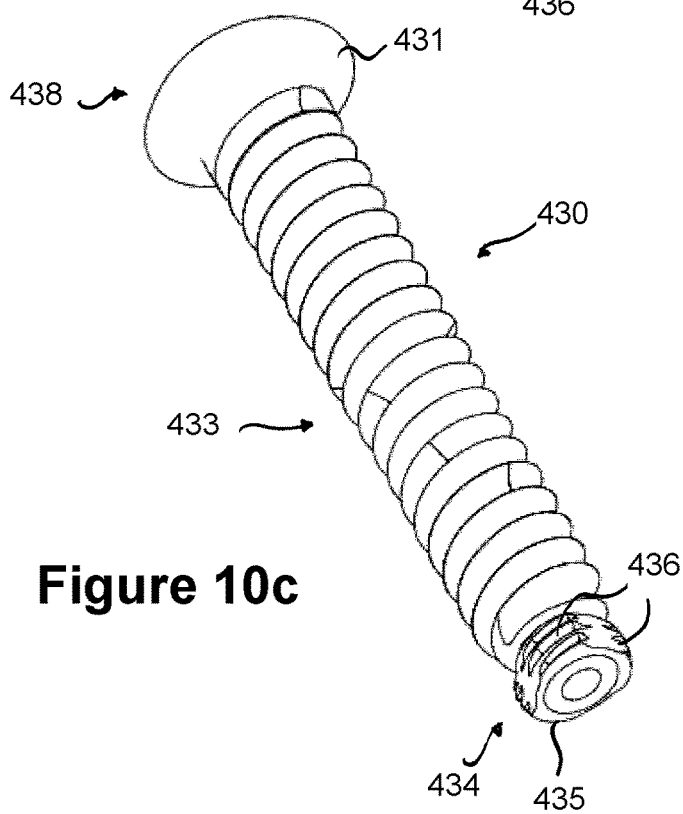
Figure 10D:
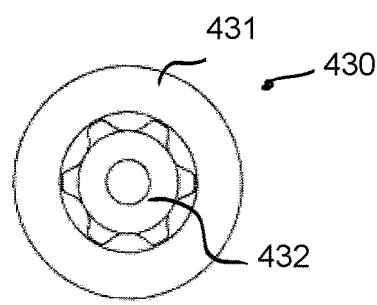
Figure 16A:
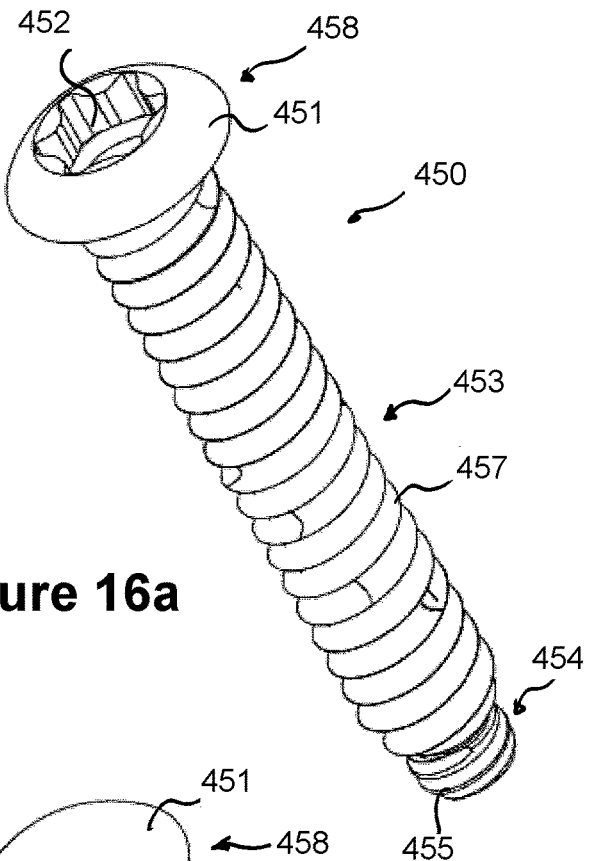
Figure 16B:
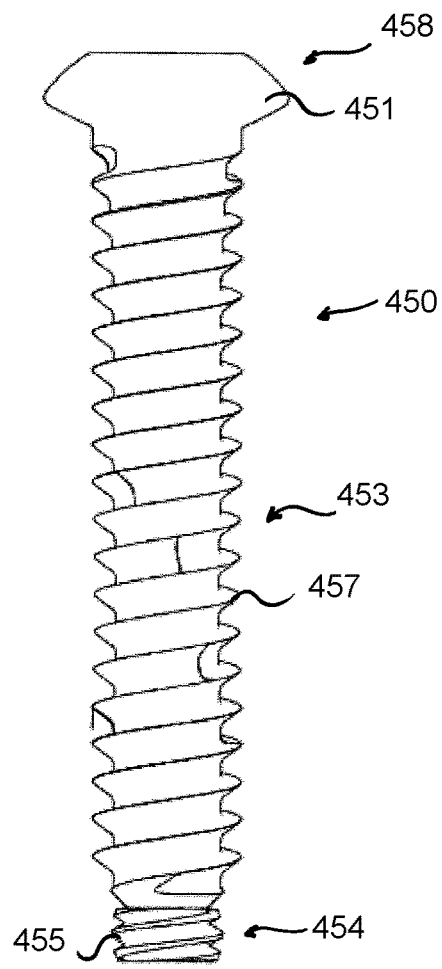
Figure 16C:
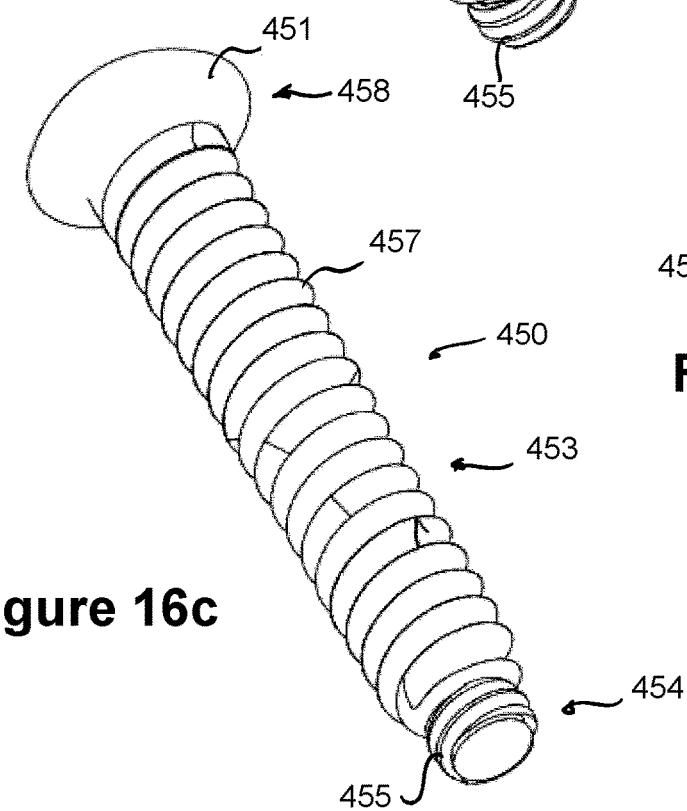
Figure 17A:
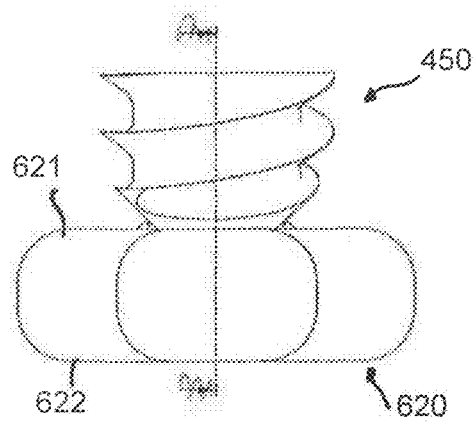
Figure 18A:
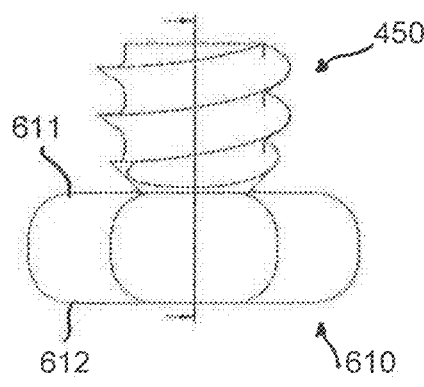
Figure 19A:
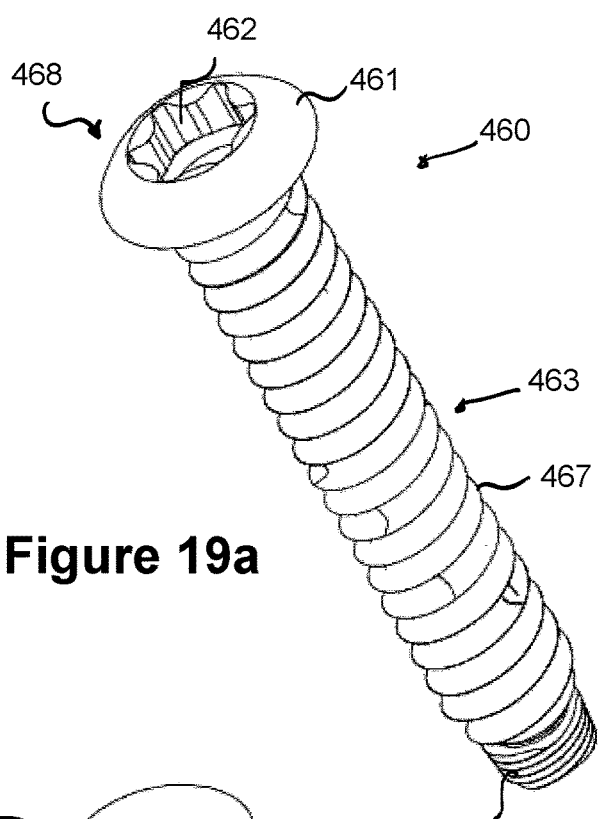
Figure 19B:
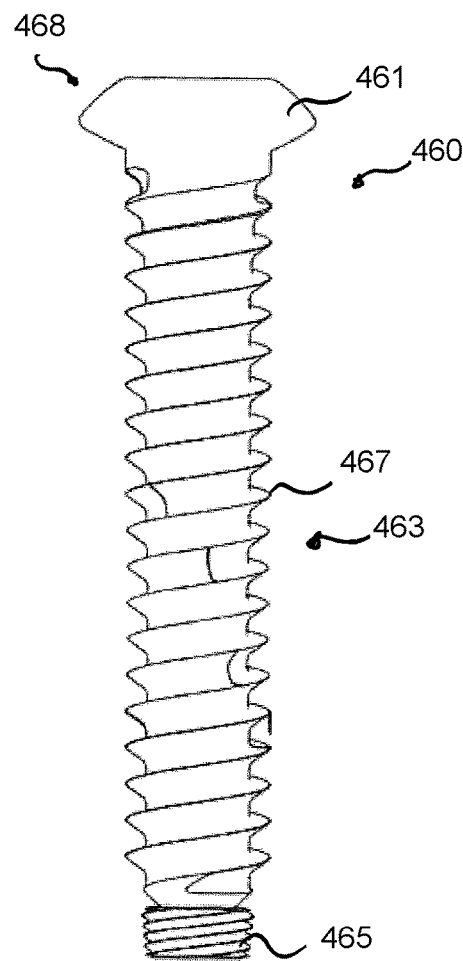
Figure 19C:
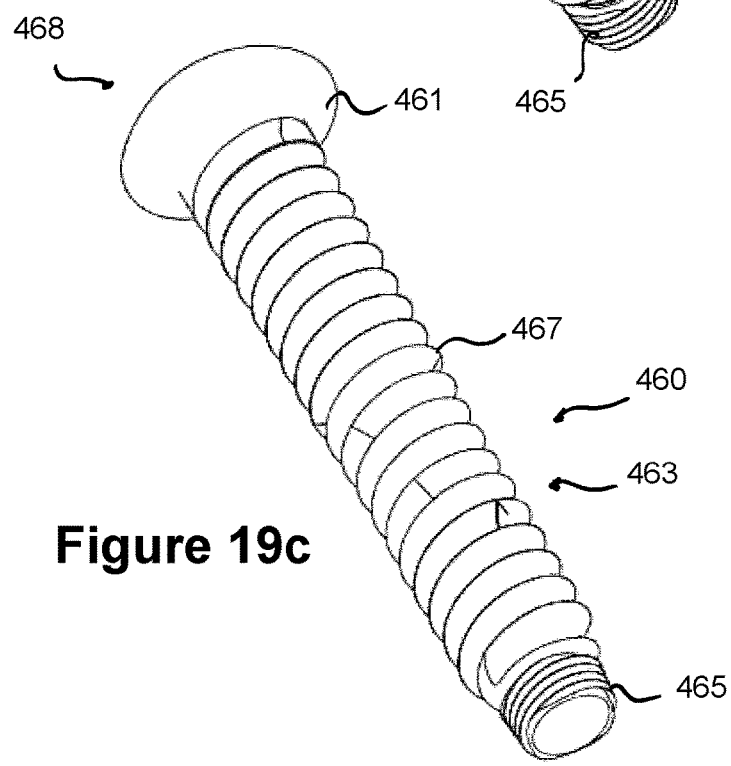
Figure 21A:
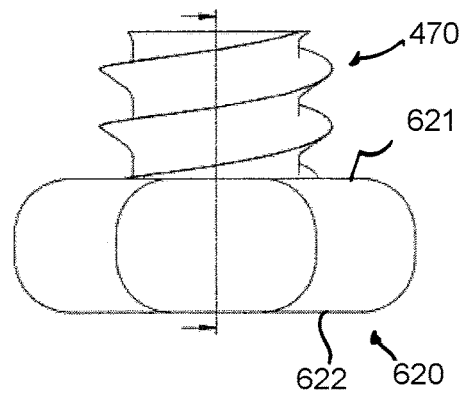
Figure 22A:
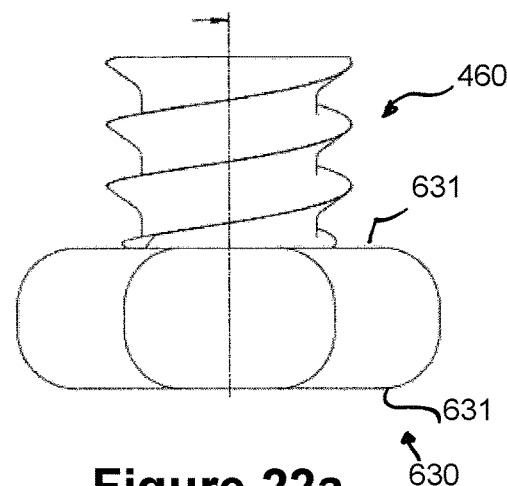

The invention is explained in detail below by way of several exemplary embodiments, in which:

FIG. 1: shows a panoramic X-ray view of a human mandible with a bone plate fastened thereon;

FIG. 2*a*: shows a perspective view of the bone plate according to FIG. 1;

FIG. 2*b*: shows a perspective view of a detail of the bone plate;

FIG. 3*a*: shows a top view of the bone plate;

FIG. 3*b*: shows a sectional view of the bone plate along the cutting line E-E shown in FIG. 3*a*;

FIG. 4*a*: shows a perspective view of a known bone screw;

FIG. 4*b*: shows a top view of the known bone screw shown in FIG. 4*a*;

FIGS. 5*a* and *b*: show two views of a first bone screw according to the invention with a screw head and a blocking element arranged at the tip;

FIGS. 6*a* and *b*: show two views of a second bone screw according to the invention without a screw head, but with a blocking element arranged at the tip;

FIGS. 7*a* to *c*: show three perspective views of a surgical set according to the invention with a bone plate and four bone screws;

FIGS. 8*a* to *c*: show three views of a detail of a further bone plate with an opening with two receiving regions;

FIGS. 9*a* to *c*: show three views of a detail of yet another bone plate with an opening with two receiving regions;

FIGS. 10*a* to *d*: show four views of a third bone screw according to the invention containing a blocking element with three clamping surfaces and a cannula;

FIGS. 11*a* to *c*: show three views of a fourth bone screw according to the invention with a blocking element with a spherical outer contour;

FIGS. 12*a* to *d*: show four views of a bone plate with a conical opening;

FIGS. 13*a* and *b*: show the bone screw from FIGS. 11*a* to *c* fixed to the bone plate from FIGS. 12*a* to *d*;

FIGS. 14*a* to *d*: show four views of a bone plate with a conical opening containing a thread;

FIGS. 15*a* and *b*: show the bone screw from FIGS. 11*a* to *c* fixed to the bone plate from FIGS. 14*a* to *d*;

FIGS. 16*a* to *c*: show three views of a fifth bone screw according to the invention with a blocking element having a spherical outer surface containing a thread;

FIGS. 17*a* and *b*: show the bone screw from FIGS. 16*a* to *c* fixed to the bone plate from FIGS. 14*a* to *d*;

FIGS. 18*a* and *b*: show the bone screw from FIGS. 16*a* to *c* fixed to the bone plate from FIGS. 12*a* to *d*;

FIGS. 19*a* to *c*: show three views of a sixth bone screw according to the invention with a blocking element with an essentially conical outer surface containing a thread;

FIGS. 20*a* to *c*: show three views of a seventh bone screw according to the invention with a blocking element with an essentially cylindrical outer surface containing a thread;

FIGS. 21*a* and *b*: show the bone screw from FIGS. 20*a* to *c* fixed to the bone plate from FIGS. 14*a* to *d*;

FIGS. 22*a* and *b*: show the bone screw from FIGS. 19*a* to *c* fixed to the bone plate having an opening with a circumferential ridge;

FIGS. 23*a* to *d*: show four views of an eighth bone screw according to the invention with a blocking element having a spherical outer surface, a conical inner opening and slots;

FIGS. 24*a* to *c*: show three views of a bone plate with a part-spherical opening;

FIGS. 25*a* to *c*: show three views of a K wire with a conically widening tip;

FIGS. 26*a* to *c*: show three steps of a method using the bone plate from FIGS. 24*a* to *c*, the bone screw from FIGS. 23*a* to *d* and the K wire from FIGS. 25*a* to *c*;

FIGS. 27*a* to *d*: show four views of a bone nail with a transversal bore having an inner thread for receiving a bone screw;

FIGS. 28*a* and *b*: show the bone screw from FIGS. 11*a* to *c* extending through a bone and through the bone nail from FIGS. 27*a* to *d* and fixed to the bone plate from FIGS. 12*a* to *d*;

FIGS. 29*a* to *c*: show three views of a ninth bone screw according to the invention with a first shank portion having a thread with a first, larger diameter and a second shank portion having a blocking element with a thread having a second, smaller diameter;

FIGS. 30*a* to *d*: show four views of a bone nail with a transversal conical bore for receiving a bone screw;

FIGS. 31*a* to *d*: show four views of a bone plate with an opening having an inner thread, namely a bone thread;

FIGS. 32*a* and *b*: show the bone screw from FIGS. 29*a* to *c* extending through a bone and through the bone nail from FIGS. 30*a* to *d* and fixed to the bone plate from FIGS. 31*a* to *d*;

FIGS. 33*a* to *d*: show four views of a bone plate with a conical opening containing several radial indentations;

FIGS. 34*a* to *d*: show four views of a bone plate with a conical opening containing a thread and several radial indentations;

FIG. 35*a*: shows a partial side view of the bone screw from FIGS. 11*a* to 11*c*;

FIG. 35*b*: shows a partial side view of a tenth bone screw according to the invention containing a blocking element with an outer contour having portions of different radii.

FIG. 1 shows a human mandible 113 with a corpus 142 and two ascending ramuses 112. For clearer representation, a projection similar to a dental panoramic X-ray view has been chosen where the outside surface of the mandible 113 has been shifted to the drawing plane. A bone plate 101' is contacted and fastened on the mandible 113. The bone plate 101 includes a main portion 109 which has a first end 143 and an oppositely situated second end 148. The main portion 109 additionally has a first contact surface which cannot be seen here and on which the main portion 109 is contacted and fastened on the corpus 142 (see FIG. 2*a* in this respect). In addition, the main portion 109 has a plurality of receiving means 108, 108' with a circular opening 102, 102' for receiving a bone screw which is not shown here (see, for example, FIGS. 4*a* and 4*b*, 10*a* to 10*d*, 11*a* to 11*c*, 16*a* to 16*c*, 19*a* to 19*c*, 20*a* to 20*c*, 23*a* to 23*d* or 29*a* to 29*c* in this respect).

The main portion 109 also comprises two wings 110 on the first end 143. Only one single wing 110 is arranged on the oppositely situated second end 148. Said wings 10 have a second contact surface, which is not shown here, for contacting and fastening on an outside surface of one of the ascending ramuses 112. In addition, the wings 110 have receiving means 145 with a circular opening 146 for receiving a bone screw which is not shown here (see, for example, FIGS. 4*a* and 4*b*, 10*a* to 10*d*, 11*a* to 11*c*, 16*a* to 16*c*, 19*a* to 19*c*, 20*a* to 20*c*, 23*a* to 23*d* or 29*a* to 29*c* in this respect).

The bone plate 101' consists of a biocompatible implant material, such as, for example, titanium and its alloys, implant steel, implantable plastics material or implantable ceramic.

FIG. 2*a* shows a perspective view of the bone plate 101' according to FIG. 1. The main portion 109 has a first contact surface 141 for contacting and fastening on the corpus 142, and the two wings 110 include in each case a second contact surface 144 for contacting and fastening on the ascending ramus 112.

Each of the openings 102, 102' and 146 has a structure which can be seen in the view of a detail according to FIG. 3*b*. The opening 102 serves for receiving a first bone screw 301 which is shown in FIGS. 4*a* and 4*b*. The opening 102 passes through the bone plate 101 along a longitudinal axis L from a first surface 202 of the bone plate 101 to an oppositely situated second surface 203 of the bone plate 101. On the first surface 202, the opening 102 opens out into a first receiving region 204 which is delimited by a first inside wall 205. On the second surface 203, the opening 102 opens out into a second receiving region 206 which is delimited by a second inside wall 207.

Three recesses 208 are formed in the circumferential direction in the first inside wall 205. In each of said three recesses 208, the distance to the first inside wall 205 increases in dependence on the angle of rotation about the longitudinal axis L. In addition, in the exemplary embodiment shown here, the first inside wall 205 is realized in a spherical manner in the region of each of the recesses 208. As an alternative to this, however, the first inside wall 205 can also be realized, for example, in a paraboloid, ellipsoid or hyperboloid manner. In an analogous manner, three recesses 209 are formed in the circumferential direction in the second inside wall 207. In each of said three recesses 209, the distance to the second inside wall 207 increases in dependence on the angle of rotation about the longitudinal axis L. In addition, in the exemplary embodiment shown here, the second inside wall 207 is realized in a spherical manner in the region of each of the recesses 209, but, as an alternative to this, could also be realized, for example, in a paraboloid, ellipsoid or hyperboloid manner. The first receiving region 204 also includes a spherical depression 210 for receiving a connecting element, in particular a screw head, of a bone screw which is not shown here. In addition, the first recess 204 has an outlet contour 212 which serves for removing a bone screw.

The two receiving regions 204, 206 are realized for a blocking means which rotates in the same direction. More precisely, both receiving regions 204, 206 are realized for a right-rotating blocking means. A blocking element of a bone screw can therefore be fixed both in the first receiving means 204 in the direction of view from the first surface 202 to the second surface 203 by rotating the bone screw clockwise and can be fixed in the second receiving region 206 in the direction of view from the second surface 203 to the first surface 202 by rotating the bone screw anticlockwise.

FIG. 3*a* shows a top view of the bone plate 101'. As can be seen in the sectional view according to FIG. 3*b*, the second receiving region 206 also includes a spherical depression 211 and an outlet contour 213.

FIGS. 4*a* and 4*b* show a known bone screw 301 which can be inserted at a variable angle in each of the openings 102, 102' and 146. Said bone screw 301 is identical to the one disclosed in WO 2004/086990. It comprises a screw shank 320 with a thread 321 as well as a screw head 310 which is realized as a blocking element and protrudes outwardly above the screw shank 320 and the thread 321. The screw head 310 comprises an engagement contour 311 in which, for example, a screwdriver can be inserted in order to insert or remove the bone screw 301. In addition, the screw head 310 is provided with a circumferential outside surface which extends substantially in the direction of a longitudinal axis K of the bone screw 301 and comprises three clamping surfaces 330 which are distributed uniformly in the circumferential direction. In alternative embodiments, the clamping surfaces 330 may not be distributed uniformly in the circumferential direction. When viewed in an azimuth plane perpendicular to the longitudinal axis K, the clamping surfaces 330 widen outwardly in a wedge-shaped manner and away from the longitudinal axis K. The outside surface is realized in a spherical manner in the region of the clamping surface 330. Said clamping surfaces 330 make it possible for the screw head 310 to be able to be blocked electively with the first inside wall 205 or the second inside wall 207, just as is described in detail in WO 2004/086990 (which simply discloses, however, an opening with one single receiving region as disclosed here).

In this way, the bone screw 301 is able to be inserted both through the opening 102 from the first surface 202 in the direction of the second surface 203 and be fixed in this manner at a variable angle in the bone plate and inserted through the opening 102 from the second surface 203 in the direction of the first surface 202 and be fixed in this manner at a variable angle in the bone plate. Consequently, both the first surface 202 and the second surface 203 can serve electively as contact surfaces which are contacted onto the bone. The bone plates can consequently be used electively and according to requirement for left-sided or right-sided defects without having to dispense with fixing at a variable angle. This clearly reduces the range of bone plates to be held ready.

Figure 5B:
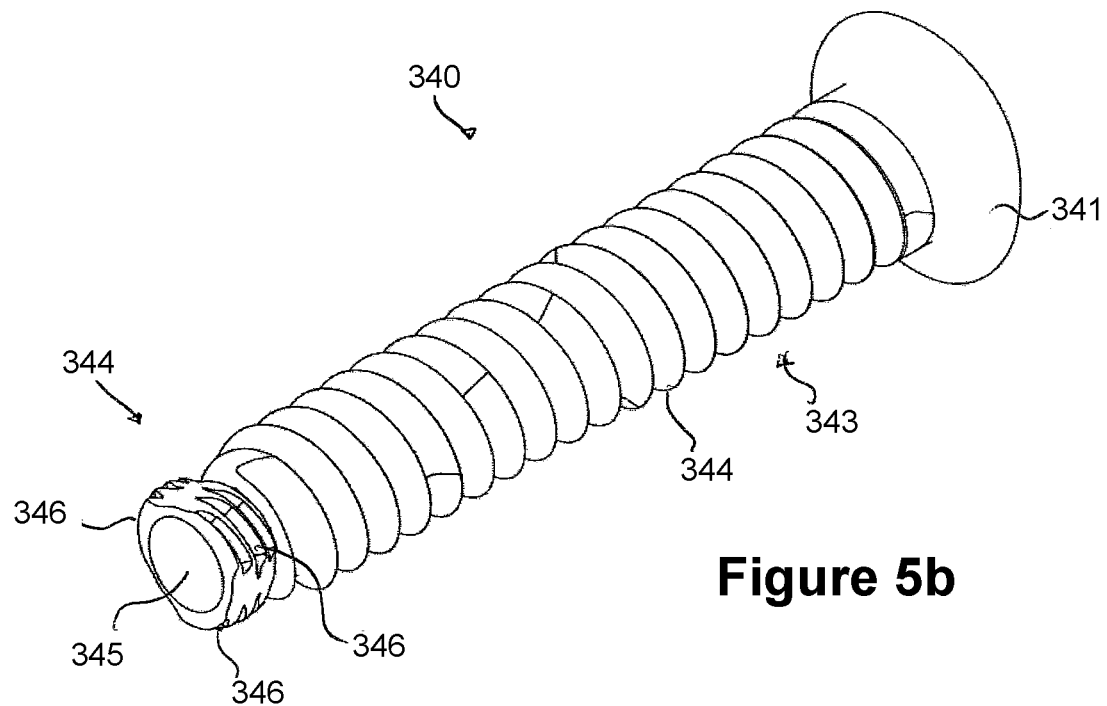

FIGS. 5*a* and 5*b* show a first bone screw 340 according to the invention. It includes a screw head 341 with an engagement contour 342, a screw shank 343 with a thread 347 and a blocking element 345 which is arranged on an end 344 of the bone screw 340 which is situated opposite the screw head 341. Said blocking element 345 includes three clamping surfaces 346 which are distributed uniformly in the circumferential direction and are realized as disclosed in WO 2004/086990.

Figure 6B:
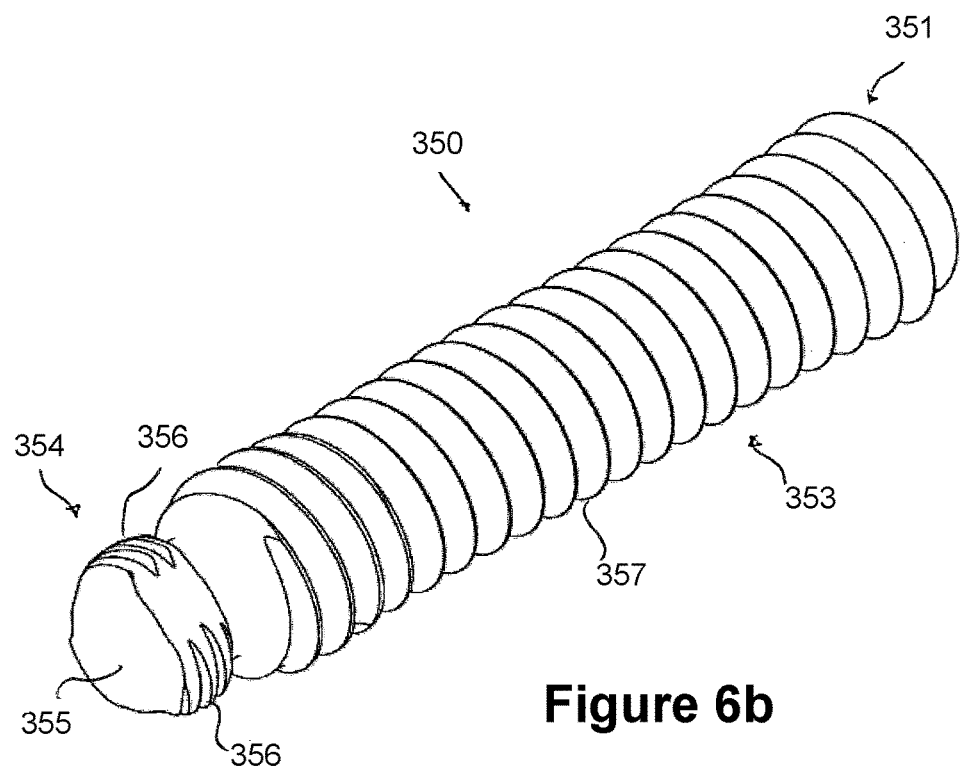

FIGS. 6*a* and 6*b* show a second bone screw 350 according to the invention which, however, does not comprise a screw head. On a first end 351 it has an engagement contour 352 and on a second end 354 which is situated opposite the first end 351 it comprises a blocking element 355 which has three clamping surfaces 356 just as the blocking element 345 shown in FIGS. 5*a* and 5*b*. A screw shank 353 with a thread 357 extends between the first end 351 and the second end 354.

FIGS. 7a to 7c show the bone plate 101' from FIG. 1 with two bone screws 340 which are shown in FIGS. 5a and 5b as well as two bone screws 301 which are shown in FIGS. 4a and 4b.

In the view according to FIG. 7a, the shorter bone screws 301 according to FIGS. 4a and 4b are inserted from the first surface 202 of the bone plate 101' in the direction of the second surface 203 and pass through the openings 102'. The bone screws 340 according to FIGS. 5a and 5b are directed with their ends 344 toward the second surface 203, but are not yet in contact therewith. In the position according to FIG. 7b, the bone screws 340 are inserted and fixed in the openings 102 by means of the blocking elements 345. FIG. 7c includes a perspective view of the first surface 202 of the bone plate 101'.

If sufficient fixing cannot be achieved just with the shorter bone screws 301, the longer bone screws 340 can provide additional stability. For example, the shorter bone screws 301 can pass through the bone plate 101' and then from the outside into a mandible, and the longer bone screws 340 can pass through the mandible completely from inside to outside and then engage in the bone plate 101'. A conceivable indication is the degradation of a bone which can occur, for example, as a result of previous radiotherapy.

In situations when soft tissue prevents a placement of bone screws through the bone plate 101' in the direction from the first surface 202 to the second surface 203, the shorter bone screws 301 may be dispensed with, and only the longer bone screws 340 may be used, which are then passed through a bone and then into the bone plate 101' in the direction from the second surface 203 to the first surface 202.

FIGS. 8a to 8c show details of a further bone plate 360, a perspective view of which is shown in FIG. 8a, a top view of which is shown in FIG. 8b and a sectional view of which is shown in FIG. 8c along the cutting line which is marked in FIG. 8b. The bone plate 360 includes an opening 361 which opens out into a first receiving region 364 on a first surface 362 of the bone plate 360 and opens out into a second receiving region 366 on a second surface 363. Both the first receiving region 364 and the second receiving region 366 include a cone-shaped internal thread 367 or rather 368 which widens in the direction of the first surface 362 or rather the second surface 363. In said exemplary embodiment, both internal threads 367, 368 are identical to one another. For example, the blocking element 445 of the bone screw 440 as shown in FIGS. 11a to 11c can be received and fixed in both receiving regions 364, 366.

FIGS. 9a to 9c show details of a further bone plate 370, a perspective view of which is shown in FIG. 9a, a top view of which is shown in FIG. 9b and a sectional view of which is shown in FIG. 9c along the cutting line which is marked in FIG. 9b. The bone plate 370 includes an opening 371 which opens out into a first receiving region 374 on a first surface 372 of the bone plate 370 and opens out into a second receiving region 376 on a second surface 373. Both the first receiving region 374 and the second receiving region 376 include a cone-shaped internal thread 377 or rather 378 which widens in the direction of the first surface 372 or rather the second surface 373. In said exemplary embodiment, only the opening angles of the two internal threads 377, 378 are identical; the first internal thread 377, however, is higher than the second internal thread 378.

For example, the blocking element 445 of the bone screw 440 as shown in FIGS. 11a to 11c can be received and fixed in both receiving regions 374, 376.

FIGS. 10a to 10d show a third bone screw 430 according to the invention in a first perspective view, a side sectional view, a second perspective view and a top view, respectively. As the bone screw 340 shown in FIGS. 5a and 5b, it includes a first end 438 having a screw head 431 with an engagement contour 432, a screw shank 433 with a thread 437 and a blocking element 435 which is arranged on a second end 434 of the bone screw 430 which is situated opposite the screw head 431. Said blocking element 435 includes three clamping surfaces 436 which are distributed uniformly in the circumferential direction and are realized as disclosed in WO 2004/086990. Unlike the bone screw 340, the bone screw 430 contains a cannula 439 extending along a longitudinal axis L of the bone screw 430.

FIGS. 11a to 11c show a fourth bone screw 440 according to the invention in a first perspective view, a side view and a second perspective view, respectively. It includes a first end 448 having a screw head 441 with an engagement contour 442, a screw shank 443 with a thread 447 and a blocking element 445 which is arranged on a second end 444 of the bone screw 440 which is situated opposite the screw head 441. Said blocking element 445 is provided with a circumferential outside surface containing a portion which is spherical.

FIGS. 12a to 12d show a bone plate 610 in a first perspective view, a side sectional view, a second perspective view and a top view, respectively, wherein the side sectional view in FIG. 12b is along the line marked in FIG. 12d. The bone plate 610 contains a first surface 611 and an opposite second surface 612 and an opening 613 penetrating the bone plate 610 from the first surface 611 to the second surface 612. The opening 613 is delimited by an inside wall 614 having an inner contour for receiving and fixing a blocking element a bone screw as shown below. The inner contour is conical.

FIGS. 13a and 13b show the bone screw 440 from FIGS. 11a to 11c fixed to the bone plate 610 from FIGS. 12a to 12d in a side view and a side sectional view, respectively. The outer contour of the blocking element 445 is received in and fixed to the inner contour of the inner wall 614 of the opening 613. As shown in FIG. 13b, the bone screw 440 is received and fixed in the opening 613 at an angle with respect to the bone plate 610, wherein this angle by be varied.

FIGS. 14a to 14d show a bone plate 620 in a first perspective view, a side sectional view, a second perspective view and a top view, respectively, wherein the side sectional view in FIG. 14b is along the line marked in FIG. 14d. The bone plate 620 contains a first surface 621 and an opposite second surface 622 and an opening 623 penetrating the bone plate 620 from the first surface 621 to the second surface 622. The opening 623 is delimited by an inside wall 624 having an inner contour for receiving and fixing a blocking element of a bone screw as shown below. The inner contour is essentially conical and contains a thread 625.

FIGS. 15a and 15b show the bone screw 440 from FIGS. 11a to 11c fixed to the bone plate 620 from FIGS. 14a to 14d in a side view and a side sectional view, respectively. The outer contour of the blocking element 445 is received in and fixed to the circumferential ridge 637.

FIGS. 16a to 16c show a fifth bone screw 450 according to the invention in a first perspective view, a side view and a second perspective view, respectively. It includes a first end 458 having a screw head 451 with an engagement contour 452, a screw shank 453 with a thread 457 and a blocking element 455 which is arranged on a second end 454 of the bone screw 450 which is situated opposite the screw head 451. Said blocking element 455 is provided with a circumferential outside surface containing a portion which is essentially spherical and contains a thread.

Figure 17B:
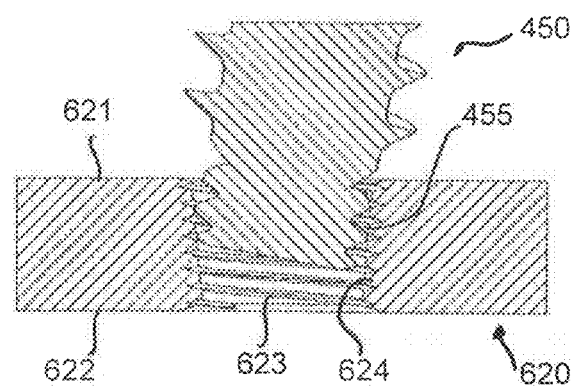

FIGS. 17a and 17b show the bone screw 450 from FIGS. 16a to 16c fixed to the bone plate 620 from FIGS. 14a to 14d in a side view and a side sectional view, respectively. The outer contour of the blocking element 455 is received in and fixed to the inner contour of the inside wall 624 of the opening 623.

Figure 18B:
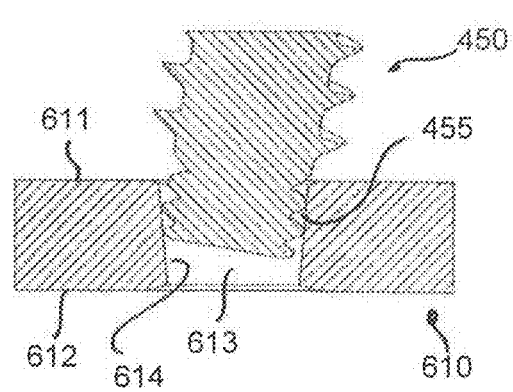

FIGS. 18a and 18b show the bone screw 450 from FIGS. 16a to 16c fixed to the bone plate 610 from FIGS. 12a to 12d in a side view and a side sectional view, respectively. The outer contour of the blocking element 455 is received in and fixed to the inner contour of the inside wall 614 of the opening 613.

FIGS. 19a to 19c show a sixth bone screw 460 according to the invention in a first perspective view, a side view and a second perspective view, respectively. It includes a first end 468 having a screw head 461 with an engagement contour 462, a screw shank 463 with a thread 467 and a blocking element 465 which is arranged on a second end 464 of the bone screw 460 which is situated opposite the screw head 461. Said blocking element 465 is provided with a circumferential outside surface containing a portion which is essentially conical and contains a thread.

FIGS. 20a to 20c show a seventh bone screw 470 according to the invention in a first perspective view, a side view and a second perspective view, respectively. It includes a first end 478 having a screw head 471 with an engagement contour 472, a screw shank 473 with a thread 477 and a blocking element 475 which is arranged on a second end 474 of the bone screw 470 which is situated opposite the screw head 471. Said blocking element 475 is provided with a circumferential outside surface containing a portion which is essentially cylindrical and contains a thread.

Figure 21B:
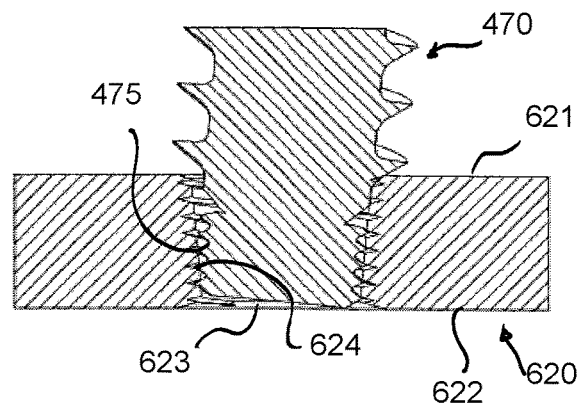

FIGS. 21a and 21b show the bone screw 470 from FIGS. 20a to 20c fixed to the bone plate 620 from FIGS. 14a to 14d in a side view and a side sectional view, respectively. The outer contour of the blocking element 475 is received in and fixed to the inner contour of the inside wall 624 of the opening 623.

Figure 22B:
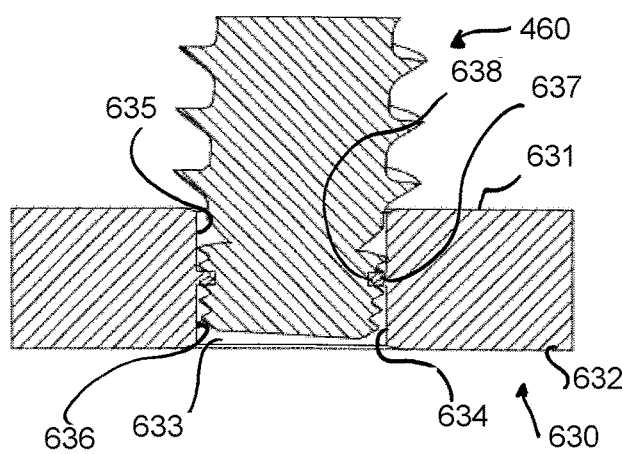

FIGS. 22a and 22b show the bone screw 460 from FIGS. 19a to 19c fixed to a bone plate 630 in a side view and a side sectional view, respectively. The bone plate 630 contains a first surface 631 and an opposite second surface 632 and an opening 633 penetrating the bone plate 630 from the first surface 631 to the second surface 632. The opening 633 is delimited by an inside wall 634 having an inner contour for receiving and fixing a blocking element of a bone screw as shown below. The inner contour contains an upper cylindrical portion 635 and a lower cylindrical portion 636 of a first, larger diameter as well as a middle cylindrical portion 638 of a second, smaller diameter formed by an inwardly directed circumferential ridge 637. The outer contour of the blocking element 465 is received in and fixed to the inner contour of the inside wall 624 of the opening 623.

In a variant of the embodiment shown in FIGS. 22a and 22b, the upper portion 635 and the lower portion 636 may be both conical and the blocking element of the bone screw may be essentially cylindrical and contain a thread.

FIGS. 23a to 23d show a eighth bone screw 480 according to the invention in a first perspective view, a second perspective view, a side sectional view and a top view, respectively. It includes a first end 488 having a screw head 481 with an engagement contour 482, a screw shank 483 with a thread 487 and a blocking element 485 which is arranged on a second end 484 of the bone screw 480 which is situated opposite the screw head 481. The bone screw 480 contains a cannula 489 extending along a longitudinal axis L of the bone screw 480. The blocking element 485 is hollow and surrounds a conical inner end portion of the cannula 489. It is provided with a circumferential outside surface containing a portion which is essentially spherical but contains four slots 486 which substantially extend in the longitudinal direction L of the bone screw 480. In alternative embodiments, the circumferential outside surface may contain between one and three or more than four slots.

FIGS. 24a to 24c show a bone plate 630 in a perspective view, a side sectional view and a top view, respectively, wherein the side sectional view in FIG. 24b is along the line marked in FIG. 24c. The bone plate 630 contains a first surface 631 and an opposite second surface 632 and an opening 633 penetrating the bone plate 630 from the first surface 631 to the second surface 632. The opening 633 is delimited by an inside wall 634 having an inner contour for receiving and fixing a blocking element of a bone screw as shown below. The inner contour contains a spherical portion.

FIGS. 25a to 25c show a K-wire 700 containing a conical tip 701.

FIGS. 26a to 26c show an application of the bone screw 480, the bone plate 630 and the K-wire 700. The K-wire 700 is received in the cannula 489 of the bone screw 480 and its conical tip 701 is received in the conical inner end portion of the cannula 489 which widens towards a mouth of the cannula 489. In this state, the bone screw 480 and the K-wire 700 are inserted such that the blocking element 485 is contained in the opening 633. Pulling the K-wire 700 along the longitudinal direction of the bone screw 480 causes an expansion of the blocking element 485. Due to this expansion, the blocking element 485 is fixed in the opening 633 of the bone plate 630.

In an alternative embodiment, the K-wire may have a cylindrical tip, and the hollow blocking element may surround an inner end portion of the cannula which narrows towards a mouth of the cannula. A contact between the cylindrical tip and the conical inner end portion of the cannula causes an expansion of the blocking element when the K-wire is pushed along the longitudinal direction of the bone screw. Due to this expansion as well, the blocking element can be fixed in an opening of the bone plate as well.

FIGS. 27a to 27d show a bone nail 710 in a first perspective view, a side sectional view, a second perspective view and a top view, respectively, wherein the side sectional view in FIG. 27b is along the line marked in FIG. 27d. The bone nail 710 contains a head 711 and a shank 712 having a non-circular cross section. The shank 712 contains a threaded bore 713 extending perpendicular to a longitudinal axis L of the bone nail 710.

FIGS. 28a and 28b show an application of the bone screw 440, the bone nail 710 and the bone plate 610 to a bone B. The threaded shank 443 of the bone screw 440 is interlocked with the threaded bore 713 of the bone nail 710 inside the bone B. The blocking element 445 of the bone screw 440 is fixed to an opening of the bone plate 610, which is situated on the opposite side of the bone B with respect to the screw head 441. This insertion of the bone screw 440 from above is particularly useful when soft tissue located below the bone plate 610 must not be perforated.

FIGS. 29a to 29c show a fourth bone screw 490 according to the invention in a first perspective view, a side view and a second perspective view, respectively. It includes a first end 498 having a screw head 491 with an engagement contour 492, a screw shank 493 with a thread 497 and a blocking element 495 which is arranged on a second end 494 of the bone screw 490 which is situated opposite the screw head 491. The blocking element 495 is provided with a circumferential outside surface containing a portion which is essentially cylindrical and has a thread. In addition, the bone screw 490 contains a further blocking element 499 which is arranged between the first end 498 and the second end 494 of the bone screw 490. The further blocking element 499 is provided with a circumferential outside surface containing a portion which is spherical. Instead of an essentially cylindrical portion with a thread, the blocking element 495 may, for example, also contain at least one clamping surface as disclosed in WO 2004/086990.

FIGS. 30a to 30d show a bone nail 720 in a first perspective view, a side sectional view, a second perspective view and a top view, respectively, wherein the side sectional view in FIG. 30b is along the line marked in FIG. 30d. The bone nail 720 contains a head 721 and a shank 722 having a non-circular cross section. The shank 722 contains a conical bore 723 extending perpendicular to a longitudinal axis L of the bone nail 720. In a variant, the bore 723 may also contain a thread.

FIGS. 31a to 31d show a bone plate 640 in a first perspective view, a side sectional view, a second perspective view and a top view, respectively, wherein the side sectional view in FIG. 31b is along the line marked in FIG. 31d. The bone plate 640 contains a first surface 641 and an opposite second surface 642 and an opening 643 penetrating the bone plate 640 from the first surface 641 to the second surface 642. The opening 643 is delimited by an inside wall 644 having an inner contour for receiving and fixing a blocking element of a bone screw as shown below. The inner contour contains a thread, in particular a bone thread.

FIGS. 32a and 32b show an application of the bone screw 490, the bone nail 720 and the bone plate 640 to a bone B. The threaded shank 493 of the bone screw 490 is interlocked with the conical bore 723 of the bone nail 720 inside the bone B. The blocking element 495 of the bone screw 490 is fixed to an opening of the bone plate 610, which is situated on the opposite side of the bone B with respect to the screw head 491. This insertion of the bone screw 490 from above is particularly useful when soft tissue located below the bone plate 640 must not be perforated.

FIGS. 33a to 33d show a bone plate 650 in a first perspective view, a side sectional view, a second perspective view and a top view, respectively, wherein the side sectional view in FIG. 33b is along the line marked in FIG. 33d. The bone plate 650 contains a first surface 651 and an opposite second surface 652 and an opening 653 penetrating the bone plate 650 from the first surface 651 to the second surface 652. The opening 653 is delimited by an inside wall 654 having an inner contour for receiving and fixing a blocking element of a bone screw. The inner contour is essentially conical but is interrupted by six indentations 655 that extend in a radial direction with respect to a longitudinal axis L of the opening 653 of the bone plate 650. In alternative embodiments, the inner contour may be interrupted by between one and five or by more than six indentations.

FIGS. 34a to 34d show a bone plate 660 in a first perspective view, a side sectional view, a second perspective view and a top view, respectively, wherein the side sectional view in FIG. 34b is along the line marked in FIG. 34d. The bone plate 660 contains a first surface 661 and an opposite second surface 662 and an opening 663 penetrating the bone plate 660 from the first surface 661 to the second surface 662. The opening 663 is delimited by an inside wall 664 having an inner contour for receiving and fixing a blocking element of a bone screw. The inner contour is essentially conical but contains a thread and is interrupted by six indentations 665 that extend in a radial direction with respect to a longitudinal axis L of the opening 663 of the bone plate 660. In alternative embodiments, the inner contour may be interrupted by between one and five or by more than six indentations.

FIG. 35a shows a partial side view of the bone screw 440 from FIGS. 11a to 11c, and FIG. 35b shows a partial side view of a tenth bone screw 550 according to the invention. On the one hand, the blocking element 445 of the bone screw 440 is provided with a circumferential outside surface containing a portion which is spherical and has a radius R. On the other hand, the blocking element 505 of the bone screw 550 is provided with a circumferential outside surface containing three portions 506, 507, 508 which are each spherical and have respective radii R1, R2 and R3.

The invention claimed is:

1. A bone screw comprising a first end having an engagement contour, wherein the engagement contour is arranged for engagement with a tool for inserting or removing the bone screw, and a second end which is situated opposite the first end and on which at least three blocking elements are arranged, wherein each of the at least three blocking elements is provided with a circumferential outside surface which comprises at least one clamping surface which when viewed in an azimuth plane perpendicular to a longitudinal axis of the bone screw widens outwardly in a wedge-shaped manner away from the longitudinal axis.

2. The bone screw as claimed in claim 1, wherein the circumferential outside surface is realized in an at least approximately spherical, paraboloid, ellipsoid or hyperboloid manner at least in the region of the clamping surface.

3. The bone screw as claimed in claim 1, wherein the bone screw contains a cannula extending along a longitudinal axis of the bone screw.

4. A surgical set including:
at least one bone screw comprising a first end having an engagement contour, wherein the engagement contour is arranged for engagement with a tool for inserting or removing the bone screw, and a second end which is situated opposite the first end and on which a blocking element is arranged, wherein the blocking element is provided with a circumferential outside surface having an outer contour with an interrupted thread, at least one bone plate including at least one opening which is at least partially delimited by an inside wall having an non-uniform inner contour for receiving and fixing the blocking element of the bone screw,
wherein the outer contour, in its initial state, is substantially different from the inner contour, in its initial state,
wherein the outer contour contains at least one slot which substantially extends in a longitudinal direction of the bone screw.

5. The surgical set as claimed in claim 4, wherein the outer contour contains at least one portion which is essentially cylindrical.

6. The surgical set as claimed in claim 4, wherein the outer contour contains at least one portion which is essentially spherical.

7. The surgical set as claimed in claim 4, wherein the outer contour contains at least one portion which is essentially conical.

8. The surgical set as claimed in claim 4, wherein the outer contour contains a thread.

9. The surgical set as claimed in claim 4, wherein the inner contour contains at least one portion which is essentially conical.

10. The surgical set as claimed in claim 4, wherein the inner contour contains at least one portion which is essentially spherical.

11. The surgical set as claimed in claim 4, wherein the inner contour contains at least one portion which is essentially cylindrical.

12. The surgical set as claimed in claim 4, wherein the inner contour contains a thread.

* * * * *